United States Patent
Huang et al.

(10) Patent No.: US 7,572,612 B2
(45) Date of Patent: Aug. 11, 2009

(54) METHOD OF PRODUCTION OF PARA-HYDROXYCINNAMIC ACID USING A THERMOSTABLE TAL ENZYME

(75) Inventors: Lixuan Lisa Huang, Hockessin, DE (US); Zhixiong Xue, Chadds Ford, PA (US); Michael P. McCluskey, Bear, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 285 days.

(21) Appl. No.: 11/485,558

(22) Filed: Jul. 12, 2006

(65) Prior Publication Data
US 2008/0213846 A1 Sep. 4, 2008

(51) Int. Cl.
C12P 7/42 (2006.01)
C12N 1/20 (2006.01)

(52) U.S. Cl. ............... 435/146; 435/252.3; 435/252.33

(58) Field of Classification Search .................. None
See application file for complete search history.

(56) References Cited

U.S. PATENT DOCUMENTS

| | | | |
|---|---|---|---|
| 6,368,837 | B1 | 4/2002 | Gatenby et al. |
| 6,521,748 | B2 | 2/2003 | Tang |
| 6,951,751 | B2 | 10/2005 | Breinig et al. |
| 2004/0059103 | A1 | 3/2004 | Huang et al. |
| 2005/0148054 | A1 | 7/2005 | Qi et al. |
| 2005/0260724 | A1 | 11/2005 | Ben-Bassat et al. |

FOREIGN PATENT DOCUMENTS

| | | |
|---|---|---|
| WO | 02090523 A2 | 11/2002 |
| WO | 2006099207 A2 | 9/2006 |

OTHER PUBLICATIONS

Chica et al. Curr Opin Biotechnol. Aug. 2005; 16(4):378-84.*
Xue, Zhixiong et al., Identification, characterization and functional expression of tyrosine ammonia-lyase and it mutants from the photosynthetic bacterium *Rhodobacter sphaeroides*, Journal of Industrial Microbiology & Biotechnology, 2007, p. 599-604, vol. 34, Springer.
Xue, Zhixiong et al., Improved production of p-hydroxycinnamic acid from tyrosine using a novel thermostable phenylalanine/tyrosine ammonia lyase enzyme, Enzyme and Microbial Technology, 2007, p. 58-64, vol. 42, Elsevier Inc.
International Search Report, International Application No. PCT/US2007/014884, International Filing Date Jun. 26, 2007.
P.M. Dey, Plant Biochemistry, 1997, Academis Press (Book Not Included).
Rabah Benfrief et. al., Monoterpene Alkaloids, Iridoids and Phenylpropanoid Glycosides From *Osmanthus austrocaledonica*, Phytochemistry, 1998, vol. 47:825-832.
R.J. Bandoni et. al., Phenylalanine and Tyrosine Ammonia-Lyase Activity in Some Basidiomycetes, Phytochemistry, 1968, vol. 7:205-207.
Koichia Ogata et. al., Metabolism of Aromatic Acid in Microorganisms Part I. Formation of Cinnamic Acid From Phenylalanine, Arg. Biol. Chem., 1967, vol. 31:200-206.
A.V. Emes et. al., Partial Purification and Properties of L-Phenylalanine Ammonia-Lyase From *Streptomyces verticillatues*, Can. J. Microbiology, 1970, vol. 48:613-622.
Kenneth R. Hanson et. al., The Enzymic Elimination of Ammonia, The Enzymes, $3^{rd}$ Edition, 1967, pp. 75-167.
J.A. Kyndt et. al., Characterization of a Bacterial Tyrosine Ammonia Lyase, a Biosynthetic Enzyme for the Photoactive Yellow Protein, FEBS Letter, 2002, vol. 512:240-244.
Kenneth R. Hanson et. al., Phenylalanine Ammonia-Lyase, Biochemistry of Plants, 1981, vol. 7:577-625.
National Center for Biotechnology Information General Identifier No. 4127289, Apr. 15, 2005, U. Nehls et. al., Sugar and Nitrogen-Dependent Regulation of an *Amanita muscaria* Phenylalanine Ammonium Lyase Gene.
U Nehls et. al., Sugar and Nitrogen-Dependent Regulation of an *Amanita muscaria* Phenylalanine Ammonium Lyase Gene, Journal of Bacteriology, 1999, vol. 181:1931-1933.
National Center for Biotechnology Information General Identifier No. 15824531, Oct. 2, 2001, S.H. Kim et. al., Cloning and Disruption of a Phenylalanine Ammonia-Lyase Gene From *Ustilago maydis*.
National Center for Biotechnology Information General Identifier No. 19168847, Mar. 1, 2002, A.A. Gatenby et. al., Bioproduction of Para-Hydroxycinnamic Acid.

* cited by examiner

*Primary Examiner*—Jon P Weber
*Assistant Examiner*—Mohammad Younus Meah

(57) ABSTRACT

A thermostable TAL enzyme was identified from the fungus *Phanerochaete chrysosporium*, which has high activity at temperatures of 40° C. to about 60° C. The enzyme was produced in engineered cells and used for production of para-hydroxycinnamic acid (pHCA) from tyrosine. When the pHCA production reaction was run at high temperature, the enzyme was more active and pHCA was produced more rapidly, making the reaction more efficient.

23 Claims, 8 Drawing Sheets

SEQUENCE LISTING

<160> NUMBER OF SEQ ID NOS: 14

<210> SEQ ID NO 1
<211> LENGTH: 737
<212> TYPE: PRT
<213> ORGANISM: Phanerochaete chrysosporium

<400> SEQUENCE: 1

```
Met Pro Ser Arg Ile Asp Tyr Tyr Thr Ser Gly Asn Gly Tyr Ala
1               5                   10                  15

Gln Ser Arg Lys Ser Ser Ala Ile Tyr Pro Ala Ser Ala Ser Thr Gly
                20                  25                  30

His Ala Ala Pro Ser Thr Glu Arg Lys Pro Glu Leu Leu Asp Lys Phe
            35                  40                  45

Val Glu Ala Tyr Asp Glu Leu Gln Ser Tyr Arg Glu Gly Lys Pro Val
        50                  55                  60

Ile Val Asp Gly His Asn Leu Ser Ile Pro Ala Val Ala Ala Thr Ala
65                  70                  75                  80

Arg Phe Gly Ala Ala Val Val Leu Asp Glu Asn Pro Glu Thr His Glu
                85                  90                  95

Arg Val Leu Gln Ser Arg Arg Val Ile Val Asp Lys Val Ser Thr Gln
            100                 105                 110

Arg Ser Val Tyr Gly Val Ser Thr Gly Phe Gly Gly Ser Ala Asp Thr
        115                 120                 125

Arg Thr Ser Asp Pro Leu Gln Leu Gly His Ala Leu Leu Gln His Gln
    130                 135                 140

His Val Gly Val Leu Pro Thr Gln Thr Glu Ser Pro Leu Pro Ala Leu
145                 150                 155                 160

Pro Leu Gly Asp Pro Leu Ala Thr Thr Ser Met Pro Glu Ala Trp Val
                165                 170                 175

Arg Gly Ala Ile Leu Ile Arg Met Asn Ser Leu Ile Arg Gly His Ser
            180                 185                 190

Gly Val Arg Trp Glu Leu Ile Glu Lys Met Gly Glu Leu Leu Arg Glu
        195                 200                 205

Asn Ile Thr Pro Leu Val Pro Leu Arg Gly Ser Ile Ser Ala Ser Gly
    210                 215                 220

Asp Leu Ser Pro Leu Ser Tyr Ile Ala Gly Thr Leu Ile Gly Ser Pro
225                 230                 235                 240

Ala Ile Arg Val Phe Asp Gly Pro Ala Ser Tyr Gly Ala Arg Arg Ile
                245                 250                 255

Leu Pro Ser Asn Ile Ala Leu Ala Asn His Gly Val Ala Pro Ile Pro
            260                 265                 270

Leu Ser Ser Lys Glu His Leu Gly Ile Leu Asn Gly Thr Ala Phe Ser
        275                 280                 285

Ala Ser Val Gly Ala Leu Ala Leu Asn Glu Ala Val His Leu Ser Leu
    290                 295                 300

Leu Ala Gln Val Cys Thr Ala Met Gly Thr Glu Ala Met Ile Gly Ala
305                 310                 315                 320

Val Gly Ser Phe Asp Ala Phe Ile His Asp Thr Ala Arg Pro His Pro
                325                 330                 335

Gly Gln Val Glu Val Ala Arg Asn Val Arg Thr Leu Leu Glu Asp Ser
            340                 345                 350

Gln Met Ala Val Lys Ala Glu Asp Glu Val His Ile Ala Glu Asp Glu
```

```
            355                 360                 365
Gly Glu Leu Arg Gln Asp Arg Tyr Pro Leu Arg Thr Ala Ala Gln Phe
    370                 375                 380

Leu Gly Pro Gln Ile Glu Asp Ile Leu Ser Ala His Glu Thr Val Thr
385                 390                 395                 400

Leu Glu Cys Asn Ser Thr Thr Asp Asn Pro Leu Ile Asp Gly Glu Thr
            405                 410                 415

Gly Thr Val His His Gly Gly Asn Phe Gln Ala Met Ala Val Thr Asn
                420                 425                 430

Ala Met Glu Lys Thr Arg Leu Ala Ile His Ile Gly Lys Leu Leu
            435                 440                 445

Phe Ala Gln Ala Thr Glu Leu Ile Asn Pro Met Met Asn Arg Gly Leu
    450                 455                 460

Pro Pro Asn Leu Ala Ala Thr Asp Pro Ser His Asn Tyr Phe Ala Lys
465                 470                 475                 480

Gly Val Asp Ile His Leu Ala Ala Tyr Val Gly Glu Leu Gly Phe Leu
            485                 490                 495

Ala Ser Pro Val Ser Ser His Ile Gln Ser Ala Glu Met His Asn Gln
                500                 505                 510

Ala Val Asn Ser Leu Ala Leu Val Ser Ala Arg Tyr Thr Ile Ser Ala
            515                 520                 525

Leu Asp Val Leu Ser Leu Leu Thr Ala Ala Tyr Leu Tyr Val Leu Cys
    530                 535                 540

Gln Ala Leu Asp Leu Arg Ala Met His Asn Asp Leu Gln Ser Ser Leu
545                 550                 555                 560

Ser Ala Ile Val Arg Glu Leu Leu Pro Lys His Phe Pro Ser Ala Ala
            565                 570                 575

Lys Arg Ala Asp Ala Leu Leu Pro Ile Leu Glu Arg Thr Ile Phe Arg
                580                 585                 590

Ala Leu Asn Ser Ser Ser Ser Ala Asp Cys Lys Ala Arg Met Val Ser
            595                 600                 605

Val Ala Ala Ser Thr Thr Thr Pro Leu Val Asp Phe Leu Ser Ala Asp
    610                 615                 620

Ala Ala Leu Ala Ser Glu Leu Ala Asn Ile Thr Ala Phe Arg Thr Glu
625                 630                 635                 640

Leu Ala Thr Arg Ala Ala Asp Ala Leu Thr Thr Leu Arg Thr Gln Tyr
            645                 650                 655

Leu Glu Gly Ala Arg Gly Ala Ala Pro Ala Ser Lys Tyr Leu Gly Lys
                660                 665                 670

Thr Arg Pro Val Tyr Glu Phe Val Arg Val Thr Leu Asn Val Pro Met
            675                 680                 685

His Gly Arg Glu Asn Leu His Asn Phe Glu Met Gly Pro Gly Val Glu
    690                 695                 700

Asp Gly Ile Ile Gly Asn Asn Ile Ser Thr Ile Tyr Glu Ala Ile Arg
705                 710                 715                 720

Asp Gly Lys Met Gln Asn Val Val Met Gln Leu Val Lys Ser Ile Lys
            725                 730                 735

Ala

<210> SEQ ID NO 2
<211> LENGTH: 689
<212> TYPE: PRT
<213> ORGANISM: Trichosporon cutaneum
```

<400> SEQUENCE: 2

```
Met Phe Ile Glu Thr Asn Val Ala Lys Pro Ala Ser Thr Lys Ala Met
1               5                   10                  15

Asn Ala Gly Ser Ala Lys Ala Ala Pro Val Glu Pro Phe Ala Thr Tyr
            20                  25                  30

Ala His Ser Gln Ala Thr Lys Thr Val Ser Ile Asp Gly His Thr Met
        35                  40                  45

Lys Val Gly Asp Val Val Ala Val Ala Arg His Gly Ala Lys Val Glu
    50                  55                  60

Leu Ala Ala Ser Val Ala Gly Pro Val Arg Ala Ser Val Asp Phe Lys
65                  70                  75                  80

Glu Ser Lys Lys His Thr Ser Ile Tyr Gly Val Thr Thr Gly Phe Gly
                85                  90                  95

Gly Ser Ala Asp Thr Arg Thr Ser Asp Thr Glu Ala Leu Gln Ile Ser
            100                 105                 110

Leu Leu Glu His Gln Leu Cys Gly Phe Leu Pro Thr Asp Ala Thr Tyr
        115                 120                 125

Glu Gly Met Leu Leu Ala Ala Met Pro Ile Pro Ile Val Arg Gly Ala
    130                 135                 140

Met Ala Val Arg Val Asn Ser Cys Val Arg Gly His Ser Gly Val Arg
145                 150                 155                 160

Leu Glu Val Leu Gln Ser Phe Ala Asp Phe Ile Asn Arg Gly Leu Val
                165                 170                 175

Pro Cys Val Pro Leu Arg Gly Thr Ile Ser Ala Ser Gly Asp Leu Ser
            180                 185                 190

Pro Leu Ser Tyr Ile Ala Gly Ala Ile Cys Gly His Pro Asp Val Lys
        195                 200                 205

Val Phe Asp Thr Ala Ala Ser Pro Pro Thr Val Leu Thr Ser Pro Glu
    210                 215                 220

Ala Ile Ala Lys Tyr Gly Leu Lys Thr Val Lys Leu Ala Ser Lys Glu
225                 230                 235                 240

Gly Leu Gly Leu Val Asn Gly Thr Ala Val Ser Ala Ala Ala Gly Ala
                245                 250                 255

Leu Ala Leu Tyr Asp Ala Glu Cys Leu Ala Ile Met Ser Gln Thr Asn
            260                 265                 270

Thr Val Leu Thr Val Glu Ala Leu Asp Gly His Val Gly Ser Phe Ala
        275                 280                 285

Pro Phe Ile Gln Glu Ile Arg Pro His Ala Gly Gln Ile Glu Ala Ala
    290                 295                 300

Arg Asn Ile Arg His Met Leu Gly Gly Ser Lys Leu Ala Val His Glu
305                 310                 315                 320

Glu Ser Glu Leu Leu Ala Asp Gln Asp Ala Gly Ile Leu Arg Gln Asp
                325                 330                 335

Arg Tyr Ala Leu Arg Thr Ser Ala Gln Trp Ile Gly Pro Gln Leu Glu
            340                 345                 350

Ala Leu Gly Leu Ala Arg Gln Gln Ile Glu Thr Glu Leu Asn Ser Thr
        355                 360                 365

Thr Asp Asn Pro Leu Ile Asp Val Glu Gly Gly Met Phe His His Gly
    370                 375                 380

Gly Asn Phe Gln Ala Met Ala Val Thr Ser Ala Met Asp Ser Ala Arg
385                 390                 395                 400

Ile Val Leu Gln Asn Leu Gly Lys Leu Ser Phe Ala Gln Val Thr Glu
                405                 410                 415
```

```
Leu Ile Asn Cys Glu Met Asn His Gly Leu Pro Ser Asn Leu Ala Gly
        420                 425                 430

Ser Glu Pro Ser Thr Asn Tyr His Cys Lys Gly Leu Asp Ile His Cys
        435                 440                 445

Gly Ala Tyr Cys Ala Glu Leu Gly Phe Leu Ala Asn Pro Met Ser Asn
        450                 455                 460

His Val Gln Ser Thr Glu Met His Asn Gln Ser Val Asn Ser Met Ala
465                 470                 475                 480

Phe Ala Ser Ala Arg Arg Thr Met Glu Ala Asn Glu Val Leu Ser Leu
                485                 490                 495

Leu Leu Gly Ser Gln Met Tyr Cys Ala Thr Gln Ala Leu Asp Leu Arg
        500                 505                 510

Val Met Glu Val Lys Phe Lys Met Ala Ile Val Lys Leu Leu Asn Glu
        515                 520                 525

Thr Leu Thr Lys His Phe Ala Ala Phe Leu Thr Pro Glu Gln Leu Ala
        530                 535                 540

Lys Leu Asn Thr His Ala Ala Ile Thr Leu Tyr Lys Arg Leu Asn Gln
545                 550                 555                 560

Thr Pro Ser Trp Asp Ser Ala Pro Arg Phe Glu Asp Ala Ala Lys His
                565                 570                 575

Leu Val Gly Val Ile Met Asp Ala Leu Met Val Asn Asp Asp Ile Thr
        580                 585                 590

Asp Leu Thr Asn Leu Pro Lys Trp Lys Lys Glu Phe Ala Lys Glu Ala
        595                 600                 605

Gly Asn Leu Tyr Arg Ser Ile Leu Val Ala Thr Thr Ala Asp Gly Arg
        610                 615                 620

Asn Asp Leu Glu Pro Ala Glu Tyr Leu Gly Gln Thr Arg Ala Val Tyr
625                 630                 635                 640

Glu Ala Val Arg Ser Glu Leu Gly Val Lys Val Arg Arg Gly Asp Val
                645                 650                 655

Ala Glu Gly Lys Ser Gly Lys Ser Ile Gly Ser Ser Val Ala Lys Ile
        660                 665                 670

Val Glu Ala Met Arg Asp Gly Arg Leu Met Gly Ala Val Gly Lys Met
        675                 680                 685

Phe
```

<210> SEQ ID NO 3
<211> LENGTH: 2129
<212> TYPE: DNA
<213> ORGANISM: Phanerochaete chrysosporium

<400> SEQUENCE: 3

```
atgccgcccc ttcaacagag cgcaagcccg aactcctgga caagttcgtc gaggcgtacg      60
acgagctgca atcctacagg gaaggcaagc cagtgatcgt cgacggacac aaccttagca     120
tccccgctgt cgcagcgacg gcgcgctttg gcgccgcggt ggccctcgac gagaaccccg     180
agacccacga gcgcgtcctg cagagcagac gcgtgattgt cgacaaggtc agcactcagc     240
gcagcgtata cggcgtcagc acgggcttcg gcggatccgg tacgttttgc gccgataccc     300
gcacaagcga cccgctccag ctcggccatg cctcctcca gcaccagcac gtcggcgtgc     360
tgccgactca gaccgagtcg ccgctcccag ctctgcccct gggtgaccca ctcgcaacga     420
cgagcatgcc agaggcctgg gttcgtggtg caatccttat ccgcatgaac tcccttatcc     480
gggggcactc tggtgtccgt tgggagctta tcgagaagat gggcgagttg ctgcgcgaga     540
```

```
atatcacccc acttgttccc ctgcgcggca gcatctctgc ctcgggagat ctctcgccgc    600
tctcatacat tgccggaacg ctcattggca gcccggctat ccgtgtcttt gatggccccg    660
cctcctatgg agcccgccgc atcctgccct cgaatatcgc gctcgccaac cacggtgtag    720
ccccgatccc gctctcttcc aaggagcact tgggtattct caacggcaca gcattctccg    780
cgtcggtcgg cgcactggct ctcaatgagg ctgttcacct ttctcttctc gcgcaggtct    840
gcacggcaat gggcaccgaa gcgatgattg gtgcagttgg ctcgttcgac gcctttattc    900
acgataccgc tcgcccgcac cccggccaag tcgaggtcgc tcgcaacgtc cggactctcc    960
tcgaggactc gcagatggcg gtcaaggctg aggacgaagt tcacattgcc gaggatgagg   1020
gcgagctccg tcaggaccgc tacccactcc gcacggcggc acaattcctt ggcccccaga   1080
ttgaggacat cctgtctgcc cacgagacgg tcactcttga gtgcaactcg accaccgata   1140
accctcttat tgatggcgag actgcaccg tgcaccatgg tggtaacttc caggccatgg   1200
ctgtcacgaa cgcgatggag aagacccgcc ttgccattca ccacattggc aagctgctct   1260
ttgcccaggc aaccgagctc atcaaccccca tgatgaaccg cggcctgcca cccaacctcg   1320
cggcgactga cccgtcccac aactacttcg ccaagggtat cgacattcac ctcgctgcct   1380
acgtcggcga gctcggcttc cttgccagcc cggtctcttc gcacatccag tccgcggaga   1440
tgcacaacca ggctgttaac tcgctcgccc tcgtgtctgc tcgctacacg atcagcgcgc   1500
tcgacgtcct ctctctcctc acggcggcgt acctttacgt cctctgccag gcgctcgacc   1560
tccgcgcgat gcacaacgac ctccagtcgt cgctctcggc gatcgtccgc gagctgctgc   1620
ccaagcattt cccgtctgcg gcgaagcgcg cggacgctct tttgcccatc ctcgagcgta   1680
ccatcttccg cgcactcaac tcctcgagct cggcagactg caaggcgcgc atggtcagcg   1740
tcgctgcctc gaccacgacg ccgctcgtcg acttcctctc tgcggacgct gcgctcgcat   1800
ccgagctcgc gaacatcact gccttccgca cggacctcgc gacgcgcgct gccgatgcac   1860
tcacgacgct gcgcacgcag taccttgagg gtgcccgtgg cgcggcacca gcgagcaagt   1920
acctcggcaa gacgcgccct gtgtacgagt tcgtgcgtgt caccctcaac gtgccgatgc   1980
acggccgcga gaacctgcac aacttcgaga tgggcccggg tgtcgaggac ggcatcatcg   2040
gcaacaacat ctcgacgatc tacgaggcca tccgcgacgg caagatgcag aacgtcgtca   2100
tgcagctcgt caagtctatc aaggcgtag                                     2129
```

<210> SEQ ID NO 4
<211> LENGTH: 2214
<212> TYPE: DNA
<213> ORGANISM: Phanerochaete chrysosporium

<400> SEQUENCE: 4

```
atgccgtccc gtatcgatta ctatacttct tctggtaacg gctacgcgca gagccgcaag     60
tcctccgcga tctacccggc tagcgcgtct accggtcatg ctgcaccgtc cacggagcgc    120
aagccggagc tgctggacaa gtttgttgaa gcgtatgatg aactgcagtc ttaccgtgaa    180
ggtaagccgg ttatcgttga cggccacaac ctgtctatcc cggcggtcgc tgctactgcg    240
cgttttggcg ctgctgtggt actgacgaa acccggaaa ctcacgaacg tgtcctgcag    300
agccgccgtg tgattgtcga caaagtttct acccagcgtt ctgtatacgg cgttagcacc    360
ggcttcggcg gttccgctga cactcgcacc tctgacccgc tgcaactggg ccacgcgctg    420
ctgcagcacc aacacgtcgg tgttctgccg actcagactg aaagcccgct gccagcccctg    480
```

-continued

```
ccactgggtg acccgctggc gaccacctct atgccggaag cgtgggttcg cggtgctatc    540
ctgattcgta tgaactctct gatccgtggt cactctggcg ttcgttggga actgattgag    600
aaaatgggtg agctgctgcg tgaaaacatt accccgctgg tcccgctgcg tggtagcatc    660
tctgctagcg gcgatctgtc tccgctgtcc tatatcgctg gcaccctgat tggttcccct    720
gccattcgtg tgttcgacgg tcctgcctct tacggtgcgc gtcgtatcct gccgtctaat    780
attgcgctgg ccaaccacgg tgtagcgccg atcccgctgc cttccaaaga acatctgggt    840
attctgaatg gtaccgcttt ttctgcctct gttggtgcac tggctctgaa cgaagctgtt    900
cacctgagcc tgctggcgca ggtatgcacc gcaatgggta ccgaagcgat gatcggcgca    960
gtgggcagct ttgatgcgtt catccacgat accgctcgtc cacacccggg ccaggtagag   1020
gttgcgcgta acgttcgtac cctgctggaa gactctcaga tggcagtcaa ggcagaagat   1080
gaagtacata ttgctgaaga tgagggtgag ctgcgccaag atcgttatcc gctgcgtacc   1140
gctgcgcagt tcctgggccc gcagatcgaa gacattctgt ctgcacacga gacgttaccc   1200
ctggaatgta actccaccac ggacaatcca ctgatcgacg gcgaaactgg cacggtacat   1260
catggtggca actttcaagc tatggcggtt accaacgcaa tggagaaaac ccgtctggcg   1320
atccaccaca tcggcaaaact gctgttcgcg caggccacgg aactgatcaa ccctatgatg   1380
aaccgcggcc tgccgccgaa cctggcagca accgaccctg ccacaattaa cttcgcaaaa   1440
ggtgttgata tccacctggc agcatacgtt ggcgagctgg gtttcctggc gagcccagtt   1500
tctagccaca tccagtccgc agaaatgcat aaccaggcag tgaactccct ggctctggtt   1560
tctgcgcgtt acaccatttc cgctctggat gtgctgtccc tgctgaccgc cgcatatctg   1620
tatgtcctgt gccaggccct ggatctgcgt gcgatgcaca acgatctgca gtcctctctg   1680
tccgccatcg ttcgtgaact gctgccgaag cattttccgt ctgcggctaa cgcgcagat   1740
gcactgctgc cgattctgga acgtaccatc ttccgcgcac tgaactcttc ttcctccgcg   1800
gactgcaaag cccgcatggt ttccgtggca gcttctacca ccaccccgct ggttgatttc   1860
ctgagcgccg acgctgccct ggcttccgaa ctggctaata ttactgcttt ccgtaccgaa   1920
ctggcgaccc gcgcagctga cgcactgacc accctgcgca cccagtaccct ggaaggtgct   1980
cgcggtgccg cgccagcttc taaatatctg ggcaaaactc gtccggtata cgaatttgtg   2040
cgtgtgactc tgaacgtgcc gatgcatggc cgtgaaaatc tgcacaactt cgaaatgggt   2100
ccgggtgttg aggatggcat catcggcaac aacatctcca ctatctacga agccatccgt   2160
gatggtaaaa tgcagaacgt tgttatgcag ctggttaagt ctattaaagc ctaa          2214
```

<210> SEQ ID NO 5
<211> LENGTH: 30
<212> TYPE: DNA
<213> ORGANISM: artificial sequence
<220> FEATURE:
<223> OTHER INFORMATION: primer

<400> SEQUENCE: 5

```
gatcgaattc atgccgcccc ttcaacagag                                       30
```

<210> SEQ ID NO 6
<211> LENGTH: 31
<212> TYPE: DNA
<213> ORGANISM: artificial sequence
<220> FEATURE:
<223> OTHER INFORMATION: primer

<400> SEQUENCE: 6
gatcaagctt ctacgccttg atagacttga c          31

<210> SEQ ID NO 7
<211> LENGTH: 42
<212> TYPE: DNA
<213> ORGANISM: artificial sequence
<220> FEATURE:
<223> OTHER INFORMATION: primer

<400> SEQUENCE: 7
gccattcagg ctgcgcatta tgacaacttg acggctacat ca          42

<210> SEQ ID NO 8
<211> LENGTH: 70
<212> TYPE: DNA
<213> ORGANISM: artificial sequence
<220> FEATURE:
<223> OTHER INFORMATION: primer

<400> SEQUENCE: 8
agccaagctt ggtacctccc ggggagctcc gaattcttcc tcctgttagc ccaaaaaacg          60
ggtatggaga          70

<210> SEQ ID NO 9
<211> LENGTH: 36
<212> TYPE: DNA
<213> ORGANISM: artificial sequence
<220> FEATURE:
<223> OTHER INFORMATION: primer

<400> SEQUENCE: 9
gcttgaaagc ttggctgttt tggcggatga gagaag          36

<210> SEQ ID NO 10
<211> LENGTH: 50
<212> TYPE: DNA
<213> ORGANISM: artificial sequence
<220> FEATURE:
<223> OTHER INFORMATION: primer

<400> SEQUENCE: 10
tcgggaattg aagcttaaga gtttgtagaa acgcaaaaag gccatccgtc          50

<210> SEQ ID NO 11
<211> LENGTH: 46
<212> TYPE: DNA
<213> ORGANISM: artificial sequence
<220> FEATURE:
<223> OTHER INFORMATION: linker

<400> SEQUENCE: 11
ctacaaactc ttggtacccc gtctagaact agtcaattcc cgacag          46

<210> SEQ ID NO 12
<211> LENGTH: 46
<212> TYPE: DNA
<213> ORGANISM: artificial sequence
<220> FEATURE:
<223> OTHER INFORMATION: linker

<400> SEQUENCE: 12
ctgtcgggaa ttgactagtt ctagacgggg taccaagagt ttgtag          46

<210> SEQ ID NO 13

```
<211> LENGTH: 53
<212> TYPE: DNA
<213> ORGANISM: artificial sequence
<220> FEATURE:
<223> OTHER INFORMATION: primer

<400> SEQUENCE: 13
ggacatcgca tgcgggttgc cttactggtt agcagaatga atcaccgata cgc        53

<210> SEQ ID NO 14
<211> LENGTH: 53
<212> TYPE: DNA
<213> ORGANISM: artificial sequence
<220> FEATURE:
<223> OTHER INFORMATION: primer

<400> SEQUENCE: 14
ctagcggact agttctcatg accaaaatcc cttaacgtga gttttcgttc cac        53
```

METHOD OF PRODUCTION OF PARA-HYDROXYCINNAMIC ACID USING A THERMOSTABLE TAL ENZYME

FIELD OF INVENTION

The present invention relates to the field of molecular biology and microbiology. More specifically this invention discloses the use of a fungal thermostable tyrosine ammonia lyase enzyme for production of para-hydroxycinnamic acid (pHCA).

BACKGROUND OF THE INVENTION

Para-hydroxycinnamic acid (pHCA) is a high-value, aromatic chemical compound that may be used as a monomer for the production of Liquid Crystal Polymers (LCP). LCPs are used in liquid crystal displays, and in high speed connectors and flexible circuits for electronic, telecommunication, and aerospace applications. Because of their resistance to sterilizing radiation and their high oxygen and water vapor barrier properties, LCPs are used in medical devices, and in chemical and food packaging. Due to its importance as a high value, aromatic chemical compound, chemical synthesis of pHCA is known. However, these chemical methods are expensive due to the high cost of the starting materials and the extensive product purification required. Moreover, these methods generate large amounts of unwanted byproducts.

Biological production of pHCA offers an alternative to chemical synthesis of this material. In plants, pHCA (also known as p-coumarate) is made as an intermediate for the synthesis of various secondary metabolites such as lignin [Plant Biochemistry, Ed. P. M. Dey, Academic Press, (1997)] and isoflavonoids. Phenylalanine ammonia-lyase (PAL) converts L-phenylalanine to trans-cinnamic acid (CA), which is then converted to pHCA. Methods of pHCA isolation and purification from plants are known [R. Benrief, et al., Phytochemistry, 47, 825-832; (1998)], however, these methods are time consuming and cumbersome and do not therefore provide an economical alternative to the current chemical synthesis route. PAL enzymes are also found in fungi (Bandoni et al., *Phytochemistry* 7:205-207 (1968)), yeast (Ogata et al., *Agric. Biol. Chem.* 31:200-206 (1967)), and *Streptomyces* (Emes et al., *Can. J. Microbiology* 48:613-622 (1970)), but not in *Escherichia coli* mammalian cells (Hanson and Havir In *The Enzymes*, 3$^{rd}$ ed.; Boyer, P., Ed.; Academic: New York, 1967; pp 75-167).

Some PAL enzymes, in addition to their ability to convert phenylalanine to cinnamate, can accept tyrosine as a substrate. The tyrosine ammonia lyase (TAL) activity of these enzymes directly converts tyrosine to pHCA. Generally, these enzymes have much higher PAL than TAL activities. A few enzymes with higher TAL than PAL activities have been found, including PAL/TAL enzymes from the bacterium *Rhodobacter capsulatus* (Kyndt et al., *FEBS Letters* 512:240-244 (2002)), the yeast, *Rhodotorula glutinis* (also known as *Rhodosporidium glutinis* and *Thodosporidium toruloides*; PAL/TAL58; Hanson and Havir, In *The Biochemistry of Plants*; Academic: New York, 1981; Vol. 7, pp 577-625), the yeast *Trichosporon cutaneum* (U.S. Pat. No. 6,951,751), and the bacterium *Rhodobacter sphaeroides* (US20040059103). In addition, U.S. Pat. No. 6,368,837 discloses a mutagenized *Rhodosporidium toruloides* PAL/TAL with an increased TAL/PAL activity ratio over that of the wild type enzyme. Several other mutant PAL/TAL genes that encode enzymes with enhanced TAL activity are disclosed in U.S. Pat. No. 6,521,748. Several of these enzymes with high TAL activity have been introduced into microorganisms for production of pHCA (U.S. Pat. No. 6,368,837, US20040059103 A1). These engineered microorganisms expressing TAL activity can be used in fermentation processes for production of pHCA. However, the enzymes having TAL activity used in these biocatalysts are sensitive to high temperatures. It is desirable to have a more robust enzyme with high TAL activity for production of pHCA using engineered biocatalysts. Applicants have solved the stated problem by isolating, characterizing and expressing a TAL enzyme which exhibits high levels of TAL catalytic activity at high temperatures.

SUMMARY OF THE INVENTION

The invention relates to a recombinant host cell engineered to provide regulated expression of a thermostable tyrosine ammonia lyase (TAL) gene, and a method of producing para-hydroxycinnamic acid using the thermostable TAL enzyme produced in the engineered cell. In the present method, production of the thermostable TAL enzyme is activated and the expressed enzyme is used in a reaction to convert tyrosine to para-hydroxycinnamic acid.

Accordingly the invention provides a method for the production of para-hydroxycinnamic acid comprising:
(a) providing a thermostable tyrosine ammonia lyase enzyme;
(b) contacting the enzyme of (a) with tyrosine wherein para-hydroxycinnamic acid is produced; and
(c) optionally recovering said para-hydroxycinnamic acid.

In one preferred embodiment the invention provides a method for the production of para-hydroxycinnamic acid comprising:
a) providing a recombinant host cell comprising a genetic construct encoding a thermostable tyrosine ammonia lyase enzyme operably linked to a regulated promoter wherein the regulated promoter is responsive to an inducer;
b) growing the recombinant host cell of (a) in the presence of the inducer and under conditions whereby the tyrosine ammonia lyase enzyme is produced; and
c) contacting the recombinant host cell of (b) containing the tyrosine ammonia lyase enzyme with tyrosine wherein pHCA is produced.

In an alternate embodiment the invention provides a method for the production of para-hydroxycinnamic acid comprising:
a) providing a recombinant host cell comprising:
  i) a genetic construct encoding a thermostable tyrosine ammonia lyase enzyme operably linked to a regulated promoter wherein the regulated promoter is responsive to an inducer; and
  ii) an endogenous source of tyrosine;
b) growing the recombinant host cell of (a) under conditions wherein tyrosine is produced; and
c) contacting the host cell of (a) with the inducer whereby tyrosine ammonia lyase produced, and pHCA is formed.

In another alternate embodiment the invention provides a method for the production of para-hydroxycinnamic acid comprising:
a) providing a recombinant host cell comprising a genetic construct encoding a thermostable tyrosine ammonia lyase enzyme operably linked to a regulated promoter wherein the regulated promoter is responsive to an inducer;
b) providing a tyrosine producing cell;

c) co-fermenting the recombinant host cell of (a) with the tyrosine producing cell of (b) under conditions where tyrosine is produced;

d) contacting the co-fermented cells of (c) with the inducer whereby tyrosine ammonia lyase is produced and pHCA is formed.

In another embodiment the invention provides a recombinant host cell comprising a genetic construct encoding a thermostable tyrosine ammonia lyase enzyme.

BRIEF DESCRIPTION OF THE FIGURES AND SEQUENCE DESCRIPTIONS

The invention can be more fully understood from the following detailed description, figures and the accompanying sequence descriptions, which form a part of this application.

Figure 1:
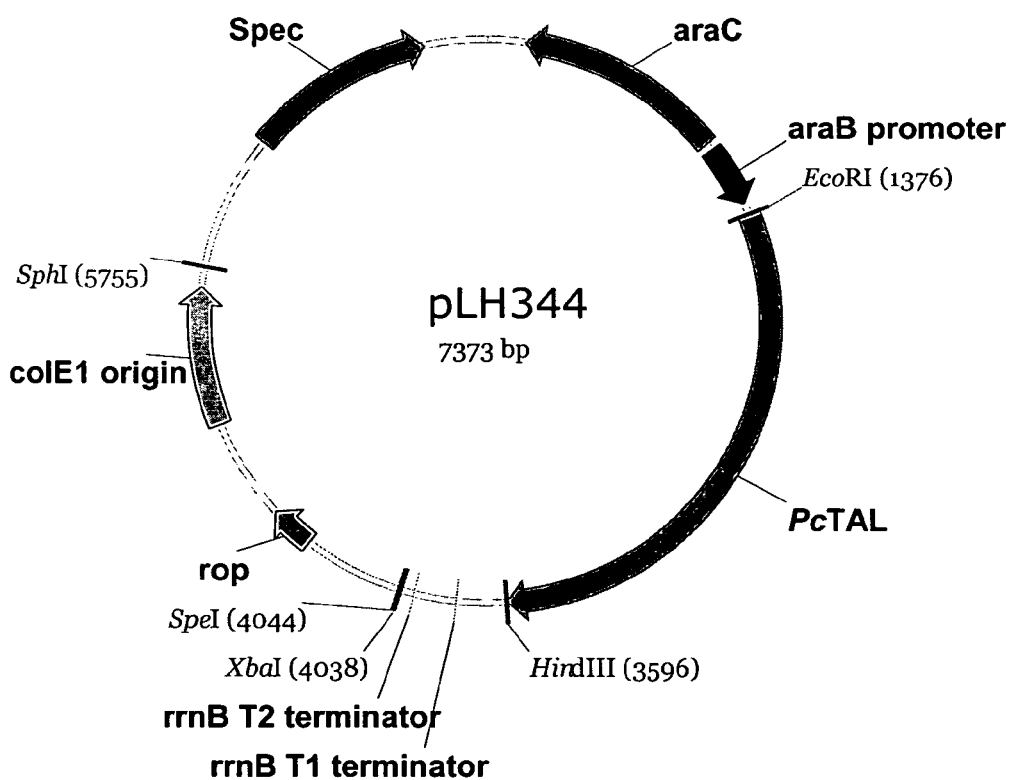
FIG. 1 shows a map of the pLH344 plasmid, which contains the codon optimized PcTAL coding region under control of an araB promoter.

The following sequences conform with 37 C.F.R. 1.821-1.825 ("Requirements for Patent Applications Containing Nucleotide Sequences and/or Amino Acid Sequence Disclosures—the Sequence Rules") and consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

A Sequence Listing is provided herewith on Compact Disk. The contents of the Compact Disk containing the Sequence Listing are hereby incorporated by reference in compliance with 37 CFR 1.52(e). The Compact Disks are submitted in triplicate and are identical to one another. The disks are labeled "Copy 1—Sequence Listing", "Copy 2—Sequence listing", and "Sequence Listing—CRF". The disks contain the following file: CL3434 seq file.ST25 having the following size: 20,000 bytes and which were created Jul. 11, 2006.

SEQ ID NO:1 is the amino acid sequence of PcTAL.

SEQ ID NO:2 is the amino acid sequence of Trichosporon cutaneum PAL/TAL.

SEQ ID NO:3 is the native DNA sequence encoding PcTAL.

SEQ ID NO:4 is the E. coli codon optimized DNA sequence encoding PcTAL.

SEQ ID NO:5 and 6 are primers for amplification of the putative TAL encoding sequence from the cDNA of P. chrysosporium.

SEQ ID NOs:7 and 8 are primers for amplification of the araC-araB region from E. coli strain FM5 (ATCC deposit no. 53911) genomic DNA.

SEQ ID NOs:9 and 10 are primers for amplification of the transcription termination sequences rrnBT1 and rrnBT2 from plasmid pTrc99A (Pharmacia Biotech, Amersham, GE Healthcare, Piscataway, N.J.).

SEQ ID NOs:11 and 12 are oligonucleotides containing a linker sequence used for site-directed mutagenesis of pLH312.

SEQ ID NOs:13 and 14 are primers for amplification of the colE1 replication origin and rop (encodes a replication origin protein) gene locus of pBR322.

DETAILED DESCRIPTION OF INVENTION

The present invention provides a method of producing pHCA that uses a thermostable tyrosine ammonia lyase/TAL) enzyme. Use of the thermostable TAL enzyme allows pHCA production to be carried out at higher temperatures than when using non-thermostable enzymes. The increase in temperature results in increased rate of pHCA production, providing a more efficient process.

pHCA is a useful monomer for production of Liquid Crystal Polymers (LCP). LCPs are polymers that exhibit an intermediate or mesophase between the glass-transition temperature and the transition temperature to the isotropic liquid or have at least one mesophase for certain ranges of concentration and temperature. The molecules in these mesophases behave like liquids and flow, but also exhibit the anisotropic properties of crystals. LCPs are used in liquid crystal displays, and in high speed connectors and flexible circuits for electronic, telecommunication, and aerospace applications. Because of their resistance to sterilizing radiation and their high oxygen and water vapor barrier properties, LCPs are used in medical devices, and in chemical and food packaging.

The following abbreviations and definitions will be used for the interpretation of the specification and the claims.

"Phenyl ammonia-lyase" is abbreviated PAL.

"Tyrosine ammonia-lyase" is abbreviated TAL.

"para-Hydroxycinnamic acid" is abbreviated pHCA.

As used herein the terms "cinnamic acid" and "cinnamate" are used interchangeably.

The term "invention" or "present invention" as used herein shall not be limited to any particular embodiment of the invention but shall refer to all the varied embodiments described by the specification ad the claims.

The term "TAL activity" refers to the ability of a protein to catalyze the direct conversion of tyrosine to pHCA. A "TAL enzyme" refers to an enzyme having TAL activity. An enzyme with TAL activity may also have PAL activity.

The term "PAL activity" refers to the ability of a protein to catalyze the conversion of phenylalanine to cinnamic acid. An enzyme with PAL activity may also have TAL activity.

The term "PAL/TAL enzyme" refers to a protein which contains both PAL and TAL activity. Such a protein has at least some specificity for both tyrosine and phenylalanine as an enzymatic substrate.

The term "PAL/TAL activity" refers to ammonia lyase enzymatic activity that is able to use both phenylalanine and tyrosine as substrates.

The term "RgTAL" refers to the *Rhodotorula glutinis* ammonia lyase enzyme that has both PAL and TAL activities. Previously this enzyme has been called *Rhodosporidium toruloides* PAL (U.S. Pat. No. 6,521,748) and *Rhodotorula glutinis* PAL or PAL/TAL. Since TAL activity is the focus in the present method, the enzyme is called RgTAL herein. Some names of genetic constructs containing DNA sequences encoding RgTAL use PAL in the name due to the PAL/TAL activity of the enzyme.

The term "thermostable TAL" refers herein to an enzyme with tyrosine ammonia lyase activity whose activity remains substantially unchanged in a crude extract, at pH8, following one hour incubation at 60° C.

The term "thermotolerant" refers to an organism that is able to grow at temperatures greater than about 37° C.

The term "co-fermentation" or "co-fermented" means the fermentive growth of more than one strain in a single fermentation system. Within the context of the present invention cells producing tyrosine may be co-fermented with cells expressing TAL enzyme for the production of pHCA.

The term "genetic construct" refers to a nucleic acid fragment that encodes for expression of one or more specific proteins. In the gene construct the gene may be native, chimeric, or foreign in nature. Typically a genetic construct will comprise a "coding sequence". A "coding sequence" refers to a DNA sequence that codes for a specific amino acid sequence.

As used herein, the terms "isolated nucleic acid molecule" and "isolated nucleic acid fragment" are used interchangeably and mean a polymer of RNA or DNA that is single- or double-stranded, optionally containing synthetic, non-natural or altered nucleotide bases. An isolated nucleic acid molecule in the form of a polymer of DNA may be comprised of one or more segments of cDNA, genomic DNA or synthetic DNA.

The term "gene" refers to a nucleic acid fragment that expresses a specific protein, including regulatory sequences preceding (5' non-coding sequences) and following (3' non-coding sequences) the coding sequence. "Native gene" or "wild type gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes.

The term "gene construct" refers to a nucleic acid fragment that encodes for expression of one or more specific proteins. In the gene construct the gene may be native, chimeric, or foreign in nature.

"Coding sequence" refers to a DNA sequence that codes for a specific amino acid sequence.

The term "expression", as used herein, refers to the transcription and stable accumulation of sense (mRNA) or antisense RNA derived from the nucleic acid fragment of the invention. Expression may also refer to translation of mRNA into a polypeptide.

The term "over-expression" as used herein, refers to the production of a gene product in transgenic organisms that exceeds levels of production in normal or non-transformed organisms.

The term "messenger RNA (mRNA)" as used herein, refers to the RNA that is without introns and that can be translated into protein by the cell.

The term "transformation" as used herein, refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The terms "plasmid", and "vector" as used herein, refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

"Expression cassette" refers to a chimeric gene having elements in addition to the coding region that allow for expression of that coding region in a host cell. The expression elements are operably linked to the coding region.

The term "host cell" refers to a cell that contains a plasmid or a vector and supports the replication or expression of the plasmid or the vector. Alternatively, foreign DNA may be may be integrated into the genome of a host cell. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing sites, effector binding sites, and stem-loop structures.

"Promoter" or "initiation control region" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments.

The term "regulated promoter" refers to a promoter that is not expressed under normal growth conditions, and is capable of being activated under specified conditions characteristic to the promoter. One type of regulated promoter is the inducible promoter that is activated in the presence of a chemical or metabolic intermediate.

The "3' non-coding sequences" or "termination control region" or "terminator" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The terms "restriction endonuclease" and "restriction enzyme" refer to an enzyme which binds and cuts within a specific nucleotide sequence within double stranded DNA.

The term "selectable marker" means an identifying factor, usually an antibiotic or chemical resistance gene, that is able to be selected for based upon the marker gene's effect, i.e., resistance to an antibiotic, wherein the effect is used to track the inheritance of a nucleic acid of interest and/or to identify a cell or organism that has inherited the nucleic acid of interest.

The term "complementary" is used to describe the relationship between nucleotide bases that are capable to hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing as well as those substantially similar nucleic acid sequences.

A nucleic acid molecule is "hybridizable" to another nucleic acid molecule, such as a cDNA, genomic DNA, or RNA molecule, when a single-stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratory Manual, 2<sup>nd</sup>* ed., Cold Spring Harbor Laboratory: Cold Spring Harbor, N.Y. (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washed with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least about 30 nucleotides. Furthermore, the skilled artisan will recognize that the temperature and wash solution salt concentration may be adjusted as necessary according to factors such as length of the probe.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humania: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences is performed using the Clustal method of alignment (Higgins and Sharp. *CABIOS*. 5:151-153 (1989)) with default parameters (GAP PENALTY=10, GAP LENGTH PENALTY=10). Default parameters for pairwise alignments using the Clustal method are: KTUPLE 1, GAP PENALTY=3, WINDOW=5 and DIAGONALS SAVED=5.

The term "codon degeneracy" refers to the degeneracy in the genetic code permitting variation of the nucleotide sequence without effecting the amino acid sequence of an encoded polypeptide.

The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "amino acid" refers to the basic chemical structural unit of a protein or polypeptide. The following abbreviations will be used herein to identify specific amino acids:

| Amino Acid | Three-Letter Abbreviation | One-Letter Abbreviation |
|---|---|---|
| Alanine | Ala | A |
| Arginine | Arg | R |

-continued

| Amino Acid | Three-Letter Abbreviation | One-Letter Abbreviation |
|---|---|---|
| Asparagine | Asn | N |
| Aspartic acid | Asp | D |
| Asparagine or aspartic acid | Asx | B |
| Cysteine | Cys | C |
| Glutamine | Gln | Q |
| Glutamine acid | Glu | E |
| Glutamine or glutamic acid | Glx | Z |
| Glycine | Gly | G |
| Histidine | His | H |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: the GCG suite of programs (Wisconsin Package, Genetics Computer Group (GCG), Madison, Wis.), BLASTP, BLASTN, BLASTX (Altschul et al., *J. Mol. Biol.* 215:403-410 (1990)), DNASTAR (DNASTAR, Inc., Madison, Wis.), and the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Publisher: Plenum, New York, N.Y.). Within the context of this application it will be understood that where sequence analysis software is used for analysis, the results of the analysis will be based on the "default values" of the program referenced, unless otherwise specified. As used herein "default values" will mean any set of values or parameters that originally load with the software when first initialized. More preferred amino acid fragments are those that are at least about 90% identical to the sequences herein using a BLASTP analysis, where about 95% is preferred. Similarly, preferred nucleic acid sequences corresponding to the sequences herein are those encoding active proteins and which are at least 90% identical to the nucleic acid sequences reported herein. More preferred nucleic acid fragments are at least 95% identical to the sequences herein.

Standard recombinant DNA and molecular cloning techniques used here are well known in the art and are described by Sambrook, J., Fritsch, E. F. and Maniatis, T. *Molecular Cloning: A Laboratory Manual*, 2$^{nd}$ ed.; Cold Spring Harbor Laboratory: Cold Spring Harbor, N.Y., 1989 (hereinafter "Maniatis"); and by Silhavy, T. J., Bennan, M. L. and Enquist, L. W. *Experiments with Gene Fusions*; Cold Spring Harbor Laboratory: Cold Spring Harbor, N.Y., 1984; and by Ausubel, F. M. et al., In *Current Protocols in Molecular Biology*, published by Greene Publishing and Wiley-Interscience, 1987.

The present invention relates to methods for production of pHCA using an enzyme with thermostable TAL activity. Cells engineered with a gene containing a regulated promoter and coding region for a thermostable TAL enzyme are grown, then the regulated promoter is activated such that the thermostable TAL enzyme is expressed and the enzyme accumulates in the cells. In one embodiment tyrosine is added to the cells with accumulated thermostable TAL, which have optionally been harvested, and pHCA is produced through TAL conversion of tyrosine to pHCA. Upon tyrosine addition, or during pHCA production, the temperature may be raised which increases the rate of pHCA production.

In another embodiment, cells producing tyrosine may be grown together with the cells harboring the thermostable TAL gene. Following sufficient cell growth for tyrosine production, the thermostable TAL gene is activated and TAL enzyme accumulates. Tyrosine produced by the co-cultured cells is converted to pHCA by the thermostable TAL. The temperature may be raised following thermostable TAL accumulation.

In yet another embodiment, the host cells harboring the thermostable TAL gene may in addition produce high levels of tyrosine. Following sufficient growth for tyrosine production, the thermostable TAL gene is activated and TAL enzyme accumulates. Tyrosine produced by the cells is converted to pHCA by the thermostable TAL. The temperature may be raised following thermostable TAL accumulation.

Thermostable TAL Coding Region and Enzyme Activity

In the present method, an enzyme with thermostable TAL activity is expressed in a recombinant cell from an isolated nucleic acid molecule encoding the enzyme. Expression of any nucleic acid molecule encoding an enzyme with thermostable TAL activity is suitable. Applicants have identified a DNA sequence from the white rot fungus *Phanerochaete chrysosporium* (*P. chrysosporium*; SEQ ID NO:3) which encodes an enzyme with TAL activity (SEQ ID NO:1) that was found to be highly thermostable. The closest known amino acid sequence is that of a PAL enzyme from the mushroom *Muscaria amanita* (GenBank CAA09013; Nehls, (1999) *J. Bacteriol.* 181 (6), 1931-1933) that has 56% amino acid identity. There is 43% identity with the *Ustilago maydis* PAL amino acid sequence (AAL09388), and 43% identity with the *R. glutinis* PAL (GenBank CAD26697; U.S. Pat. No. 6,368,837).

The *P. chrysosporium* protein was found to have both PAL and TAL activity, with a PAL/TAL ratio of 0.7. Thus the TAL activity was higher than the PAL activity, and therefore the protein is hereinafter referred to as PcTAL. Furthermore PcTAL was shown to have increasing TAL activity with increasing temperature, reaching its maximum activity at a temperature of about 60° C. in whole cells. The activity at 60° C. was about 6-fold higher than that at 25° C. in whole cells. Activity of the purified PcTAL enzyme also increased with increasing temperature. The maximum activity was reached at about 55° C., which was about 3-fold higher than that observed at 25° C. These results indicate that the PcTAL enzyme is stable and highly active at high temperatures. In general, higher enzymatic activity at higher temperatures is observed only if an enzyme is stable at those temperatures. It was found that PcTAL has activity of 1479 U/g at 55° C., and 1431 U/g at 60° C., which is much higher than the activity of a typical non-thermostable TAL enzyme at 35° C. For example, the *R. glutinis* TAL enzyme has TAL activity of 752 U/g at 35° C. DNA sequences encoding enzymes having thermostable TAL activities that may be identified in other organisms may be used in the present invention. Enzymes that are suitable include those with TAL activities that remain substantially unchanged in a crude extract, at pH8, following one hour incubation at 60° C. Thermostable TAL enzymes may be identified in thermotolerant organisms such as bacteria, filamentous fungi, yeasts, algae, and plant cells. Examples include thermotolerant strains of bacteria such as *E. coli* and other coliforms, *Gluconobacter, Schlegelella ther-*

*modepolymerans, Caenibacterium thermophilum*, lactic acid bacteria, *Campylobacteria*, and *Actinomycetes*; fungi, such as *Aspergilli, Absidia corymbifera, Acrophialophora nainiana*; yeast such as *Pichia, Candida* and *Saccharomyces*; and algae such as red alga, and *Prototheca*. DNA sequences encoding potentially thermostable TAL enzymes may be identified and isolated using the PcTAL amino acid sequence (SEQ ID NO:1) or the encoding DNA sequence (SEQ ID NO:3), and the encoded proteins assayed for thermostability. Any identified DNA sequence encoding an enzyme with TAL activity may be expressed in a host cell, typically as a component of a chimeric gene as described below herein, and the expressed enzyme may be assayed for thermostability as described in Examples herein. The enzyme activity may be assayed in whole cells that are expressing the enzyme, as described in Example 7 herein, or the enzyme may be purified from the expressing cells (Example 6 herein) and assayed, as described in Example 7 herein.

In addition, known DNA sequences encoding PAL/TAL enzymes, or known PAL/TAL enzyme amino acid sequences may be used to identify and isolate coding sequences for potentially thermostable TAL enzymes, that are then assayed for thermostability as stated above. The amino acid sequence of the *T. cutaneum* PAL/TAL enzyme may be used as described herein in Example 2. Amino acid sequences of other known PAL/TAL enzymes may also be used in homology searches of known protein sequences, or of translations of known DNA sequences. Examples of amino acid sequences that may be used include that of *R. toruloides* (WO9811205), *Rhodobacter capsulatus* (Kyndt et al., *FEBS Letters* 512:240-244 (2002)), the yeast *Rhodosporidium* (PAL/TAL58; reported in Hanson and Havir, In *The Biochemistry of Plants*; Academic: New York, 1981; Vol. 7, pp 577-625), the yeast *Trichosporon cutaneum* (US20040023357), and the bacterium *Rhodobacter sphaeroides* (US20040059103).

In addition, the DNA sequences encoding these and other known PAL/TAL enzymes may be used to identify potentially thermostable enzymes with TAL activity using methods well known to one skilled in the art. Examples of sequence-dependent protocols include, but are not limited to, methods of nucleic acid hybridization, and methods of DNA and RNA amplification as exemplified by various uses of nucleic acid amplification technologies [e. g., polymerase chain reaction (PCR), ligase chain reaction (LCR)].

For example, genes encoding enzymes with PAL/TAL activities could be isolated directly by using all or a portion of the known sequences as DNA hybridization probes to screen libraries from any desired plant, fungi, yeast, or bacteria using methodologies well known to those skilled in the art. Specific oligonucleotide probes based upon the literature nucleic acid sequences can be designed and synthesized by methods known in the art (Maniatis, supra). Moreover, the entire sequences can be used directly to synthesize DNA probes by methods known to the skilled artisan such as random primers DNA labeling, nick translation, or end-labeling techniques, or RNA probes using available in vitro transcription systems. In addition, specific primers can be designed and used to amplify a part of or full-length of the instant sequences. The resulting amplification products can be labeled directly during amplification reactions or labeled after amplification reactions, and used as probes to isolate full length cDNA or genomic fragments under conditions of appropriate stringency.

In addition, two short segments of the literature sequences may be used in polymerase chain reaction protocols, including RT-PCR, to amplify longer nucleic acid fragments encoding homologous genes from DNA or RNA. The polymerase chain reaction may also be performed on a library of cloned nucleic acid fragments wherein the sequence of one primer is derived from the literature sequences, and the sequence of the other primer takes advantage of the presence of the polyadenylic acid tracts to the 3' end of the mRNA precursor encoding bacterial genes. Alternatively, the second primer sequence may be based upon sequences derived from the cloning vector. For example, the skilled artisan can follow the RACE protocol [Frohman et al., PNAS USA 85:8998 (1988)] to generate cDNAs by using PCR to amplify copies of the region between a single point in the transcript and the 3' or 5' end. Primers oriented in the 3' and 5' directions can be designed from the literature sequences. Using commercially available 3' RACE or 5' RACE systems (BRL), specific 3' or 5' cDNA fragments can be isolated [Ohara et al., PNAS USA 86:5673 (1989)]; and [Loh et al., Science 243:217, (1989)].

Any isolated nucleic acid molecule encoding an enzyme with demonstrated thermostable TAL activity may be used in the present invention. Such enzymes may be isolated by means well known in the art as described above from organisms having tolerance to higher temperatures (thermo-tolerant organisms). Thermo-tolerant bacteria, (Adachi, et al., *Applied Microbiology and Biotechnology* (2003), 60(6), 643-653; Arfman, et al., *Microb. Growth C1 Compd.*, [Int. Symp.], 7th (1993), 267-74. Editor(s): Murrell, J. Collin; Kelly, Don P. Publisher: Intercept, Andover, UK.) thermotolerant filamentous fungi (Sekita, et al., *Microb. Biomass Proteins* (1986), 127-40. Editor(s): Moo-Young, Murray; Gregory, Kenneth F. Publisher: Elsevier Appl. Sci., London, UK.), thermotolerant yeasts (Rao et al., *Concise Encyclopedia of Bioresource Technology* (2004), 394-402. Editor(s): Pandey, Ashok. Publisher: Haworth Press, Binghamton, N.Y.), thermotolerant algae and thermotolerant plants (Viswanathan, et al., *Current Science* (1996), 71(4), 275-284) are known and provide suitable sources for these enzymes. Particularly suitable herein are nucleic acid molecules having similarity to the *P. chrysosporium* TAL enzyme as set forth in SEQ ID NO:1. The skilled person will be able to use this sequence to find related sequences having thermo-stable properties by the methods described above. Accordingly it is contemplated that useful nucleic acid molecules will be selected from the group consisting of:

(a) an isolated nucleic acid molecule encoding the amino acid sequence as set forth in SEQ ID NO:1;

(b) an isolated nucleic acid molecule that hybridizes with (a) under the following hybridization conditions: 0.1× SSC, 0.1% SDS, 65° C. and washed with 2×SSC, 0.1% SDS followed by 0.1×SSC, 0.1% SDS; and (c) an isolated nucleic acid molecule that encodes a polypeptide having 95% identity based on the Clustal method of alignment when compared to a polypeptide having the sequence as set forth in SEQ ID NO:1.

Examples of isolated nucleic acid molecule sequences encoding the *P. chrysosporium* TAL enzyme, which may be used in the present method, are the natural coding sequence (SEQ ID NO:3) and the codon optimized sequence (SEQ ID NO:4) described below.

Codon Optimization

One embodiment of the present method uses an isolated nucleic acid molecule having the sequence of SEQ ID NO:4. This sequence is codon-optimized for expression of the PcTAL in *E. coli*. Optimizing the codons for a particular host cell may enhance the translation of messenger RNA that is transcribed from a gene containing the coding sequence. *E. coli* is a particularly suitable host cell in the present method, and the natural sequence of the nucleic acid molecule encoding PcTAL is not optimal for expression in *E. coli*. Thus SEQ ID NO:4 is particularly useful as an isolated nucleic acid encoding the thermostable TAL protein which possesses the enzyme activity for use in the present process.

Recombinant Expression

An isolated nucleic acid molecule encoding a protein with thermostable TAL enzyme activity for use in the present method is operably linked to suitable regulatory sequences, typically in a chimeric gene construct, to allow expression in a recombinant host cell. Regulatory sequences include promoters and terminators for transcription, as well as translation control regions. Especially useful are regulatory sequences that direct high level expression of foreign proteins and that allow control of the timing of expression. Promoters used are regulated promoters that are not expressed under normal growth conditions, and are capable of being activated under specified conditions. Promoters which are useful to drive expression of the instant coding regions in the desired host cell are numerous and familiar to those skilled in the art, such as inducible promoters araB, rhaB, lac, tac, trc, T7, T5, tetracycline promoter, trp promoter, luxR promoter, tightly regulated synthetic promoters derived from lac/tac promoter, Int/att-mediated gene inversion-controlled promoters, acid-inducible promoters, salt inducible promoters, pHCA inducible promoters, and heat/cold inducible promoters. Particularly suitable is the araB promoter. Termination control regions may also be derived from various genes native to the preferred hosts. Optionally, a termination site may be unnecessary; however, it is most preferred if included.

A chimeric gene for expression of a thermotstable TAL enzyme is generally added to a vector that is used to make a recombinant host cell suitable for use in the present method. Vectors useful for the transformation of suitable host cells are well known by one skilled in the art. Typically the vector additionally contains sequences allowing autonomous replication or chromosomal integration and a marker. Autonomous replicating vectors are typically plasmids used in cloning and transformation procedures, which then are maintained within a recombinant cell. Vectors may also be used which promote the integration of the chimeric gene encoding a thermostable TAL into the host cell genome. Such vectors may be for either random or site-directed integration, or for homologous recombination. A vector may have features allowing single cross-over or double-crossover types of homologous recombination. Transformation of the vector into a host cell is by methods well know in the art such as uptake in calcium treated cells, electroporation, freeze-thaw uptake, heat shock, lipofection, electroporation, conjugation, fusion of protoplasts, and biolistic delivery.

The marker provides a trait for identifying cells by methods including selection and screening. The marker is used to identify those cells that receive the transforming plasmid. Types of usable markers include screening and selection markers. Many different selection markers available for recombinant cell selection may be used, including nutritional markers, antibiotic resistance markers, metabolic markers, and heavy metal tolerance markers. Some specific examples include, but are not limited to, thyA, serA, ampicillin resistance, kanamycin resistance, carbenicillin resistance, and mercury tolerance. In addition, a screenable marker may be used to identify recombinant cells. Examples of screenable markers include GFP, GUS, carotenoid production genes, and beta-galactosidase. A particularly suitable marker in the instant invention is a selectable marker.

Recombinant Cell

Recombinant cells suitable for the present method include cells that are able to express a gene that encodes a thermostable TAL enzyme. Typically cells of microorganisms are used. Microorganisms useful for the expression of a thermostable TAL in the present method may include, but are not limited to bacteria, such as the enteric bacteria (*Escherichia*, and *Salmonella*) as well as *Bacillus, Acinetobacter, Streptomyces, Methylobacter, Rhodococcus* and *Pseudomonas*; Cyanobacteria, such as *Rhodobacter* and *Synechocystis*; yeasts, such as *Saccharomyces, Zygosaccharomyces, Kluyveromyces, Candida, Hansenula, Debaryomyces, Mucor, Pichia* and *Torulopsis*; and filamentous fungi such as *Aspergillus* and *Arthrobotrys*, and algae. Thermostable TAL enzymes may be produced in these and other microbial hosts to express high amounts of TAL enzyme for production of commercially useful amounts of pHCA. The preferred host for use in the present method is *Escherichia* and the preferred strain is *E. coli* K12.

It is well known to one skilled in the art that certain genetic compositions of a host cell are required for expression of specific regulatory elements that may be present in a chimeric gene encoding a thermostable TAL. For example, when using the araB promoter, the host cell must be unable to metabolize arabinose, the inducer used to activate the araB promoter. Typically the host cell has a deletion of the araBAD operon in the chromosome. The araBAD operon may be deleted by methods well known in the art, such methods include one-step inactivation of chromosomal genes in *E. coli* K12 strains using PCR products with homologous sequences as the chromosomal DNA region adjacent to the knockout target (e.g. araBAD) [Datsenko K A et al., *Proc Natl Acad Sci USA* 97: 6640-6645 (2000)].

pHCA Production Using Thermostable TAL Enzyme pHCA is produced in the present method by contacting the thermostable TAL enzyme with tyrosine under controlled conditions of pH and temperature for a period of time to allow conversion of tyrosine to pHCA by the enzyme. Tyrosine used in the present method may be made by a recombinant cell (further described below), synthesized through a chemical reaction, or made by other methods such as purifying from a natural source, an example of which is chicken feathers. Commercially available tyrosine, such as from J. T. Baker (Phillipsburg, N.J.), may be used. Tyrosine may be used as partially or fully purified tyrosine for addition to the thermostable TAL for a pHCA production run.

Using thermostable TAL, an alkaline pH is suitable in the pHCA production reaction, as described in US20050260724 A1 which is herein incorporated by reference, since the pH optimum of the thermostable enzyme is similar to that of non-thermostable PAL/TAL enzymes. A pH that is between about 8 and about 12 is typically used. More suitable is a pH between about 9.0 and about 10.5, and most preferred are ranges of 9.5 to about 9.9.

In the present method for pHCA production, a temperature that is higher than typical cell growth conditions of 30° C. to 35° C. may be used due to the thermostability of the TAL enzyme. The TAL enzyme may be used as a purified enzyme, in a partially purified extract, or in intact cells. Particularly suitable is a biocatalyst consisting of cells containing high levels of accumulated thermostable TAL enzyme. The thermostable TAL enzyme is produced and accumulated in cells at a temperature compatible with cell growth, typically 30° C. to 35° C. Following completion of cell growth, a higher temperature is used during pHCA production. At higher temperatures the thermostable TAL enzyme has higher activity compared to the TAL enzymes that are not thermostable and will not be able to function at such high temperatures. Using the thermostable TAL enzyme, therefore, pHCA is produced at a faster rate. The thermostable enzyme of the invention will be useful at temperatures of at least 35° C. Typically, temperatures that are at least 35° C. to about 60° C. may be applied when using whole cells containing thermostable TAL as a biocatalyst. Particularly suitable are temperatures that are at least 35° C. and up to about 55° C. Most suitable are temperatures between about 40° C. and about 50° C. Conversion of tyrosine to pHCA may typically be carried out using purified TAL enzyme at temperatures of at least 35° C. and up to about 55° C., with temperatures between about 40° C. and about 50° C. being more suitable.

A benefit of using a thermostable TAL enzyme, rather than non-thermostable enzyme, at 35° C. is the stability of the enzyme for recycling the cells containing the enzyme. For pHCA production at 35° C. and at higher temperatures, the thermostable TAL enzyme may be recycled for use in multiple pHCA production runs. When using the thermostable TAL biocatalyst, recycling typically involves harvesting the biocatalyst by centrifugation following a pHCA production reaction, optionally washing the biocatalyst, and again adding tyrosine to the thermostable TAL containing biocatalyst. This recycling may be performed multiple times, until the thermostable TAL enzyme looses activity that is adequate for pHCA production.

Variations of Thermostable TAL Biocatalyst Production and Use in pHCA Production When converting tyrosine to pHCA using thermostable TAL enzyme at a temperature greater than 35° C., the temperature is raised after cells having a gene for thermostable TAL expression are grown at physiological temperature and thermostable TAL is expressed for a period of time such that the thermostable TAL protein accumulates to a high level in the cells. Thermostable TAL protein may accumulate to about 10% -50% of the total cell protein when using a strong and highly regulated promoter for thermostable TAL expression. It is particularly suitable to grow cells having a gene for thermostable TAL expression at 30° C. to 37° C. under conditions where the thermostable TAL enzyme is not expressed for a period of time to produce a large amount of these cells. Then conditions are applied for expression of the thermostable TAL enzyme. The conditions typically include adding an inducer that activates the regulated promoter that is operably linked to the coding region for the thermostable TAL so that the enzyme is produced. For example, when the coding region for thermostable TAL is linked to the araB promoter, cells are first grown without the arabinose inducer, which is then added to activate thermostable TAL enzyme production.

In one embodiment, after the thermostable TAL enzyme accumulates in the cells, tyrosine is added and the temperature is raised to the desired level for conversion of tyrosine to pHCA. In this embodiment, the tyrosine is from a source that is separate from the recombinant cell in which thermostable TAL is produced. Tyrosine may be from one of the sources described herein above, where if made in a recombinant cell, it is not the same cell that harbors the thermostable TAL gene. The recombinant cells containing the accumulated thermostable TAL enzyme may be harvested prior to contacting with tyrosine. Typically the cells are collected by centrifugation and stored as fermentation broth, as cell paste after centrifugation, or as concentrate after microfiltration and used as needed in the present method. The biocatalyst may be frozen as fermentation paste, or using standard methods including a cryoprotectant such as in glycerol or DMSO, typically at about 5° C. to –80° C.

In another embodiment, cells having a gene for thermostable TAL expression may be grown together (co-fermented) with cells that are tyrosine over-producers (described below). Both cell strains are grown under conditions where tyrosine is made, but thermostable TAL is not produced. Then expression of the thermostable TAL enzyme is activated, typically by adding inducer, and the enzyme is accumulated. The temperature is then raised, when further TAL production is not required, to the desired level for enhanced conversion of tyrosine to pHCA by the thermostable TAL.

In yet another embodiment, the cells which are able to produce thermostable TAL are also able to produce high levels of tyrosine. The cells are grown for a period of time without thermostable TAL expression but with tyrosine production. Then thermostable TAL expression is induced for production of the enzyme. Following thermostable TAL accumulation, the temperature may be raised to enhance thermostable TAL activity for pHCA production.

Recombinant Cells Producing Tyrosine

As stated above, tyrosine used in the present method may be produced by a recombinant cell other than that which produces thermostable TAL. The tyrosine may be recovered as partially or fully purified tyrosine prior to contacting thermostable TAL, or cells producing tyrosine may be grown together with the cells for thermostable TAL production. Strains of microbial cells, such as *Escherichia, Methylosinus, Methylomonas, Pseudomonas, Streptomyces, Corynebacterium, Brevibacteria, Microbacterium, Arthrobacter, Candida, Citrobacter*, and *Rhodobacter*, which are known to over-produce tyrosine, or may be genetically engineered to over-produce tyrosine, are suitable as a source of tyrosine. Examples of tyrosine over-producing strains that are suitable for the present method include, *Microbacterium ammoniaphilum* ATCC 10155, *Corynebactrium lillium* NRRL-B-2243, *Brevibacterium divaricatum* NRRL-B-2311, *Arthrobacter citreus* ATCC 11624, and *Methylomonas* SD-20. Other suitable tyrosine over-producers are known in the art, see for example *Microbial production of L-tyrosine: A Review*, T. K. Maiti et al, Hindustan Antibiotic Bulletin, vol 37, 51-65, 1995. Additionally an example of an *Escherichia* tyrosine over-producing strain that may be used is *E. coli* TY1, available from OmniGene Bioproducts, Inc. Cambridge, Mass. New strains that over-produce tyrosine may be identified, produced through mutation or genetic engineering, or otherwise obtained. Any strain that overproduces tyrosine may be used in the present method.

Alternatively, tyrosine used in an embodiment of the present method may be produced by the recombinant cell that also produces thermostable TAL. A cell which produces high levels of tyrosine may be the recipient of the thermostable TAL expression gene. Alternatively the cell harboring the thermostable TAL gene may be engineered for tyrosine production by methods such as described in commonly owned US20040248267, US 20050148054 A1 and co-pending, co-owned U.S. patent application Ser. No. 11/448,331, which are herein incorporated by reference.

Recombinant Cell Growth

Recombinant cells that harbor a gene for expression of a thermostable TAL enzyme, that over-produce tyrosine, or both, are grown in the presence of a fermentable carbon substrate in the present method. Fermentable carbon substrates may include but are not limited to monosaccharides such as glucose, raffinose and fructose, oligosaccharides such as lactose or sucrose, polysaccharides such as starch or cellulose or mixtures thereof and unpurified mixtures from renewable feedstocks such as cheese whey permeate, corn-steep liquor, sugar beet molasses, and barley malt. Additionally the carbon substrate may also be organic acids such as acetate, pyruvate and glycerol as well as one-carbon substrates such as carbon dioxide, formaldehyde, formate or methanol.

In one embodiment a large scale fermentation process is used that may be either a batch culture or a continuous culture.

A classical batch fermentation is a closed system where the composition of the medium is set at the beginning of the fermentation and not subject to alterations during the fermentation. Thus, at the beginning of the fermentation the medium is inoculated with the desired microorganism(s) and fermentation is permitted to occur adding nothing to the system. Typically, however, the concentration of the carbon source in a "batch" fermentation is limited and attempts are often made at controlling factors such as pH and oxygen concentration. In batch systems the metabolite and biomass compositions of the system change constantly up to the time the fermentation is stopped. Within batch cultures cells moderate through a static lag phase to a high growth log phase and finally to a stationary phase where growth rate is diminished or halted. If untreated, cells in the stationary phase will eventually die. Cells in the log phase generally are responsible for the bulk of production of the desired product, which in the present method is tyrosine and/or thermostable TAL.

A variation on the standard batch system is the Fed-Batch system, which may also be used. Fed-Batch fermentation processes comprise a typical batch system with the exception that the fermentable carbon substrate is added continuously or in increments as the fermentation progresses. Fed-Batch systems are useful when catabolite repression is apt to inhibit metabolism of the cells, where it is desirable to have limited amounts of substrate in the medium, or when growth to high densities is desirable. Measurement of the actual substrate concentration in Fed-Batch systems is difficult and therefore the rate of substrate consumption is estimated on the basis of the changes of measurable factors such as pH, dissolved oxygen and the partial pressure of waste gases such as CO2. Batch and Fed-Batch fermentations are common and well known in the art and examples may be found in [Brock, T. D.; *Biotechnology: A Textbook of Industrial Microbiology*, 2nd ed.; Sinauer Associates: Sunderland, Mass., 1989] or [Deshpande, M. V. *Appl. Biochem. Biotechnol.* 36:227, (1992)], herein incorporated by reference.

In addition, continuous fermentation may be used for tyrosine or TAL production. Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in their log phase of growth.

Continuous fermentation allows for modulation of any number of factors that affect cell growth or end product concentration. For example, one method will maintain a limiting nutrient such as the carbon source or nitrogen level at a limiting concentration and allow all other parameters to be in excess. In other systems a number of factors affecting growth can be altered continuously while the cell concentration, measured by the medium turbidity, is kept constant. Continuous systems strive to maintain steady state growth conditions and thus the cell loss due to the medium removal must be balanced against the cell growth rate in the fermentation. Methods of modulating nutrients and growth factors for continuous fermentation processes as well as techniques for maximizing the rate of product formation are well known in the art of industrial microbiology and a variety of methods are described by Brock, supra.

Tyrosine may be recovered from fermentation broth using low speed centrifugation. The resulting pelleted material may be suspended in water and separated again using low speed centrifugation.

Recovery of pHCA

Methods for the recovery of pHCA from a medium are available. One preferred method is taught in the copending and commonly owned U.S. patent application Ser. No. 10/824,237, hereby incorporated by reference. Briefly the method involves first acidifying the fermentation broth containing the pHCA to a pH of about 4.0 or below and then adding an extractant. Extractants useful for this purpose are water immiscible organic solvents and may include but are not limited to, methyl ethyl ketone, ethylacetate, diisopentyl ether, n-propyl benzoate, 2-undecanone, dibenzyl ether, 2-tridecanone, 2-decanone, 1-pentanone 1-phenyl, methyl decanoate, 1-undecanol, diisobutyl DBE-IB and mixtures thereof. The pHCA is dissolved in the extractant and removed from the medium. The pHCA may then be recovered from the extractant by well known means such as distillation, adsorption by resins, or separation by molecular sieves. Alternatively, the pHCA may be recovered by acidification of the growth medium to a pH below 2.0, followed by crystallization.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described, "Maniatis" supra, Enquist supra; and by Ausubel supra.

The meaning of abbreviations is as follows: "s" means second(s), "min" means minute(s), "h" means hour(s), "psi" means pounds per square inch, "nm" means nanometers, "d" means day(s), "μL" means microliter(s), "mL" means milliliter(s), "L" means liter(s), "mm" means millimeter(s), "nm" means nanometers, "mM" means millimolar, "M" means molar, "mmol" means millimole(s), "μmole" means micromole(s)", "g" means gram(s), "μg" means microgram(s) and "ng" means nanogram(s), "U" means units, "mU" means milliunits and "U/g" means units per g, "OD" means optical density, "$OD_{600}$" means the optical density measured at a wavelength of 600 nm, "ppm" means parts per million, "kD" means kilodaltons, "rpm" means revolutions per minute, "xg" means times gravity, "dcw" means dry cell weight, "SLPM" stands for standard liters per minute "CA" is cinnamic acid.

Media and Culture Conditions:

Materials and methods suitable for the maintenance and growth of bacterial cultures were found in *Experiments in Molecular Genetics* (Jeffrey H. Miller), Cold Spring Harbor Laboratory Press, Cold Spring Harbor, N.Y. (1972); *Manual of Methods for General Bacteriology* (Phillip Gerhardt, R. G. E. Murray, Ralph N. Costilow, Eugene W. Nester, Willis A. Wood, Noel R. Krieg and G. Briggs Phillips, eds), pp. 210-213, American Society for Microbiology, Washington, D.C. (1981); or Thomas D. Brock in *Biotechnology: A Textbook of Industrial Microbiology*, Second Edition (1989) Sinauer Associates, Inc., Sunderland, Mass. All reagents and materials used for the growth and maintenance of bacterial cells were obtained from Aldrich Chemicals (Milwaukee, Wis.), BD Diagnostic Systems (Sparks, Md.), Invitrogen Corp. (Carlsbad, Calif.), or Sigma Chemical Company (St. Louis, Mo.) unless otherwise specified.

LB medium contains the following in gram per liter of medium: Bacto-tryptone (10), Bacto-yeast extract, (5.0), and NaCl, (10).

Molecular Biology Techniques:

Restriction enzyme digestions, ligations, transformations, and methods for agarose gel electrophoresis were performed as described in Maniatis. Polymerase Chain Reactions (PCR) techniques were found in White, B., *PCR Protocols: Current Methods and Applications*, Volume 15 (1993) Humana Press Inc, Totowa, N.J.

HPLC Method

The mixture of phenylalanine, tyrosine, cinnamic acid and pHCA can be analyzed using the following HPLC method:

An Agilent 1100 System (Agilent technologies, Palo Alto, Calif.) with a photodiode array detector and a Zorbax SB-C18 column (3.5 µm, 4.6×150 mm—rapid resolution) is used and separation is achieved by a gradient combining two solvents: Solvent A, 0.1% trifluoroacetic acid in water; Solvent B, 0.1% trifluoroacetic acid in acetonitrile. The method requires a column flow rate of 1.0 mL/min, with a run time of 15 minutes and a post-run time of 5 minutes. The solvent gradient used is that given in Table 1 below. The pump runs within pressure limits defined as a minimum of 20 bar and a maximum of 400 bar. Solutions are filtered through a 0.45-micron nylon filter before dilution in HPLC-grade water and transfer into HPLC vial and injection. The sample spectrum is scanned from 100 nm to 380 nm, and the signal for phenylalanine at 215 or 220 nm, tyrosine at 278 nm, CA at 278 nm and pHCA at 312 nm are measured. Table 2 shows the elution times for the compounds of interest using the described method.

TABLE 1

Solvent Gradient Used for HPLC

| Time (min) | Solvent A | Solvent B |
|---|---|---|
| 0 | 95% | 5% |
| 8 | 20% | 80% |
| 10 | 20% | 80% |
| 15 | 95% | 5% |

TABLE 2

Elution times for various compounds of interest

| Compound | Elution time - min (+/−0.1) |
|---|---|
| phenylalanine | 4.4 |
| tyrosine | 3.5 |
| CA | 7.2 |
| pHCA | 5.3 |

Protein Assay

Protein concentrations were determined by the Bradford protein assay, using a BioRad kit (BioRad Laboratories, Hercules, Calif.) for protein determination. A protein standard curve was generated using five protein standard solutions ranging from 100 to 800 µg/mL bovine serum albumin (BSA).

Enzyme Activity Assay

The PAL and TAL activities of the purified enzymes were measured using a spectrophotometer according to Abell et al., [Phenylalanine Ammonia-lyase from Yeast *Rhodotorula glutinis*," *Methods Enzymol.* 142:242-248 (1987)]. The assay for PAL determination was initiated by addition of the enzyme to a 50 mM Tris-HCl (pH 8.5) buffer solution containing 1.0 mM L-phenylalanine. The reaction was followed by monitoring the CA production at λ290 nm and the activity was calculated using a molar extinction coefficient of 9000 $cm^{-1}$. The assay was run over a 5 min period using an amount of enzyme that produced absorbance changes in the range of 0.0075 to 0.018/min. One unit of activity indicated deamination of 1.0 micro-mol of phenylalanine to CA per minute. The TAL activity was similarly measured using tyrosine, instead of phenylalanine, in the reaction solution. The absorbance of the pHCA produced was followed at λ315 nm and the activity was determined using an extinction coefficient of 10,000 $cm^{-1}$ for pHCA. One unit of activity indicated deamination of 1.0 micro-mol of tyrosine to pHCA per minute. Some TAL assays were performed at pH 9.5 or 10.0 in 100 mM CAPS buffer. The TAL activity was measured as described above, except that the extinction coefficient was 16,800 $cm^{-1}$ for pHCA.

The TAL assay was typically performed in a 1.5 ml capacity UV grade disposable cuvette (VWR) at 35° C. using a Perkin-Elmer Lamba20 spectrophotometer (Wellesley, Mass.). The reaction (1.0 ml volume) contained the soluble protein sample, 100 mM CAPS pH10 buffer and 10 mM tyrosine and was monitored for 3 minutes at I315 nm. The TAL activity (U/g) was calculated as follows:

Total TAL activity (mM/min)=D315 nm/min×1,000,000 (mM/M) divided by pHCA extinction coefficient ($M^{-1}$ $cm^{-1}$)=D315 nm/min×1,000,000 (mM/M) divided by 16,800 ($M^{-1}$ $cm^{-1}$).

TAL specific activity (U/g)=total TAL activity (mM/min) divided by the amount of protein used in the assay.

Gel Electrophoresis

A 4-12% gradient BIS-TRIS gel (Invitrogen, Carlsbad, Calif.) was loaded with 4.0 µg of protein per lane, run at 200 v, and stained with Simply Blue SafeStain (Invitrogen). The High Molecular Weight (HMW) marker was used as the molecular weight standards (Amersham, GE Healthcare, Piscataway, N.J.).

Example 1

PAL/TAL Activity in Crude Extracts of *P. chrysosporium*

To identify novel PAL/TAL enzymes, four white rot fungal strains, obtained from USDA Forest Products Laboratory, *Phanerochaete chrysosporium* (ME446), *Irpex lacteus* (HHB-7328-Sp), *Trametes versicolor* (Mad-697) and *Bjerkandera adusta* (L-15259-Sp) were tested. Each fungal strain was grown in 15 g/L Difco Malt Extract Broth (Becton Dickinson Microbiology Systems, Sparks, Md.). Tyrosine (2.0 mM final concentration) was added after one-day growth at 30° C. to induce PAL/TAL activities. The cultures were then harvested after 3 days, crude extracts were prepared by bead-beating in 50 mM Tris-HCl, pH 8.5 buffer containing protease inhibitor mini tablets (Roche Biosciences, Palo Alto, Calif.), and PAL/TAL assays were carried out on the soluble crude extracts as described in General Methods. The data given in Table 3 shows that all four strains possessed PAL/TAL activities.

TABLE 3

PAL/TAL activity in crude extracts of white rot fungi.

| Species | TAL (U/g) | PAL (U/g) | PAL/TAL Ratio |
|---|---|---|---|
| *Phanerochaete chrysosporium* | 1.25 | 2.68 | 2.14 |
| *Bjerkandera adusta* | 1.25 | 1.00 | 0.80 |
| *Irpex lacteus* | 1.98 | 1.80 | 0.91 |
| *Trametes versicolor* | 2.05 | 5.83 | 2.84 |

Example 2

Identification of TAL Open Reading Frame in *P. chrysosporium* Genome

The amino acid sequence of the PAL/TAL protein from the fungus *Trichosporon cutaneum* (*T. cutaneum*; SEQ ID NO:2; disclosed in U.S. Pat. No. 6,951,751) was used in a tBLASTN search of the genomic sequence of *P. chrysosporium*. *P. chrysosporium* is a fungus with an optimum growth temperature of 40° C. The genome of *P. chrysosporium* has been sequenced and is available by contacting DOE Joint Genome Institute, US Dept. of Energy; Martinez et al. (2004) Nature Biotechnology 22, 695-700). The results revealed a region on contig 12 (1144981-1147415, on the complementary strand) that encodes amino acid fragments having extensive sequence similarity with the PAL/TAL enzyme of *T. cutaneum*. The probability that this alignment is random is $e^{-128}$, suggesting a very high level of confidence for the sequence alignment. tBlastN (Altschul et al., *J. Mol. Biol.* 215:403-410 (1990), results comparing translations in all 6 reading frames of the *P. chrysosporium* genomic sequence with the *Trichosporon cutaneum* PAL/TAL amino acid sequence (SEQ ID NO:2) as the query were generated. With introns removed, the identified *P. chrysosporium* genomic region contained a single open reading frame (e_gwh2.12.71.1) that had been annotated as a potential PAL/TAL gene based on sequence similarities to other ammonia lyases. This ORF encodes a protein having 40.7% identity to the amino acid sequence of the *T. cutaneum* PAL/TAL enzyme. The protein is referred to as PcTAL herein.

Example 3

Cloning of DNA Fragment Encoding PcTAL from *P. chrysosporium*

Total RNA was prepared from 100 ml of *P. chrysosporium* cells grown for 3 days in 15 g/L malt broth (as described in Example 1) supplemented with 2.0 mM tyrosine. Cells were harvested by centrifugation (3500 rpm, 5 min) in a Beckman CS-6R centrifuge with GH3.8 rotor (Beckman Coulter, Inc. Fullerton, Calif.), washed once with water, resuspended in 1.0 ml of Trizol reagent (Invitrogen, Carlsbad, Calif.), mixed with an equal volume of 0.5 mm glass beads, transferred to two 2.0 ml screw cap tubes and homogenized at maximum speed in a Biospec Mini beadbeater (Biospec Products, Bartlesville, Okla.) for three minutes. The homogenized cells were transferred to microfuge tubes and centrifuged at 14000 rpm in an Eppendorf centrifuge (Westbury, N.Y.). The supernatant was combined into one tube and allowed to sit for 5 minutes at room temperature. Chloroform/isoamylalcohol (0.2 ml, 25/1 mixture) was added and the tube shaken for 15 sec by hand. The solution was then incubated for 5 min at room temperature followed by centrifugation for 5 min at 14000 rpm at 4° C. The aqueous upper phase was transferred to a new tube and isopropanol (0.5 ml) was added. After 10 min at room temperature the solution was centrifuged at 14000 rpm for 5 min at 4° C., the supernatent was removed, and the RNA pellet allowed to air dry and then was dissolved in RNase free water (0.5 ml).

The total RNA sample was directly used for polyA(+)RNA isolation using the Qiagen oligoTex kit (Qiagen, Valencia, Calif.) following the manufacturer's protocol. Total RNA (0.5 ml) was mixed with 0.5 ml of buffer OBB from the kit. The Oligotex suspension (50 µl) was added, and the sample incubated at 72° C. for 5 minutes. It was then allowed to cool at room temperature for 10 min and the Oligotex:mRNA complex pelleted by centrifugation at 14000 rpm in a microfuge for 2 minutes after which the supernatant was removed, and the pellet resuspended in 400 ul of buffer OW2 from the kit. The resuspended sample was transferred into the kit's spin column and centrifuged at 14000 rpm for one minute, and washed one more time with 400 µl of buffer OW2 by resuspending the pellet and centrifugation. The mRNA was eluted by adding 25 ul of 75° C. buffer OEB from the kit followed by centrifugation for one minute. The elution step was repeated one more time. The total amount of mRNA obtained was 1.75 ug.

A first strand of cDNA was prepared from the mRNA sample using the Invitrogen 3'-RACE kit. The mRNA sample (50 ng in 11 µl) was mixed with AP primer (1.0 µl of 10 µM) from the kit, heated to 72° C. for 10 minutes followed by chilling on ice for 2 minutes. At this time 2.0 µl each of kit components, [10×PCR buffer, 25 mM $MgCl_2$, and 0.1M DTT] and 1.0 µl of 10 mM dNTP was added and the mixture placed in a 42° C. air incubator for two minutes. To this solution, superscript II reverse transcriptase (1.0 µl) was added, and the mixture incubated at 42° C. for one h. The resulting first strand cDNA was directly used as a PCR template.

The following primers were designed for amplification of the putative TAL encoding sequence from the cDNA of *P. chrysosporium*:

```
PCPAL-F:
GATCGAATTCATGCCGCCCCTTCAACAGAG      (SEQ ID NO: 5)

PCPAL-R:
GATCAAGCTTCTACGCCTTGATAGACTTGAC     (SEQ ID NO: 6)
```

The forward primer started at residue 33 of the putative ORF such that the codons for the first 11 amino acids were omitted. Because of the high GC content of the sequence, BD Bioscience Advantage GC-cDNA polymerase mix was used for amplification (Clontech, Mountain View, Calif.). The reaction mixture contained 1.0 µl of $1^{st}$ strand cDNA as template, 1.0 µl each of the 20 µM primers, 10 µl of 5.0 M GC melt, 10 µl of 5×PCR buffer, 1.0 µl of 50× dNTP mix, 1.0 µl of Advantage GC cDNA polymerase mix, and 25 µl of water. The PCR conditions used were: 94° C. 1 min 30 sec, followed by 30 cycles of 94° C. 30 sec and 68° C. 4 min. A final incubation at 68° C. for 7 minutes was added at the end. The PCR product was analyzed by agarose gel electrophoresis and a ~2.1 kb band was observed. The PCR product was then diluted 1:50, and 1.0 µl of the diluted product used as template for a second round of PCR, using TaKaRa ExTaq 2× premix and the same set of primers. The reaction volume was 50 µl and the PCR conditions were: 94° C. one min 30 sec, followed by 30 cycles of 94° C. 30 sec, 55° C. 30 sec and 72° C. two min, ending with 7 min at 72° C.

The PCR product from the second round was purified with a Qiagen PCR purification kit according to the manufacturer's protocol. The purified PCR product was digested with EcoRI and HindIII, and ligated with pBAD-HisB (Invitrogen) that was digested with the same enzymes. The EcoRI and HindIII sites in the pBAD-HisB vector are in the Multiple Cloning Site between an araB promoter and rrnB T1 and T2 terminators. The pBAD-HisB vector additionally contains a gene encoding the araC transcriptional activator, located upstream from the araB promoter, and an ampicillin resistance marker. The ligated DNA was used to transform E. coli Top 10' competent cells (Invitrogen).

Seven colonies resulting from plating the transformed cells on LB+50 µg/ml Amp medium were chosen to inoculate 2.0 ml cultures of LB+Amp 50+0.2% arabinose, which were grown overnight at 37° C., and centrifuged at 14000 rpm for two min. Typically the pHCA product produced by the TAL enzyme intracellularly can diffuse across the cell membrane, therefore the presence of pHCA in culture supernatants is an indication that the TAL enzyme is expressed in an active form in the cells. The supernatants were analyzed by HPLC as described in the General Methods for the presence of pHCA and CA. Four samples contained significant amounts of both compounds, indicating the presence of PAL/TAL activity, as shown in Table 4. These results confirmed that the cloned DNA fragment encoded a TAL enzyme.

TABLE 4

The pHCA and CA levels in the supernatants of induced P. chrysosporium TAL expression clones.

| Sample | pHCA (ppm) | CA (ppm) |
|---|---|---|
| Clone 1 | 22 | 24 |
| Clone 2 | 1 | 1 |
| Clone 3 | 0 | 0 |
| Clone 4 | 48 | 93 |
| Clone 5 | 35 | 50 |
| Clone 6 | 28 | 36 |
| Clone 7 | 1 | 1 |

Example 4

Synthesis and Subcloning of Codon Optimized DNA Sequence Encoding PcTAL

Analysis of the sequence of the cloned PcTAL encoding DNA fragment showed that the codon usage was not optimal for expression in E. coli. An E. coli codon optimized PcTAL coding region fragment was designed and synthesized by DNA2.0 (Palo Alto, Calif.). EcoRI and HindIII sites were included at the 5' and 3' ends of the designed PcTAL coding sequence, respectively. The sequence of the codon optimized coding region is given in SEQ ID NO:4. A DNA fragment containing this sequence was cloned into the vector pJ2 (DNA2.0).

The DNA fragment containing the codon optimized PcTAL coding region was subcloned into plasmid pLH320. pLH320 is a medium copy number expression vector constructed for high level inducible expression of the RgTAL coding region. pLH320 was constructed starting with pCL1920, a low copy number plasmid with the SC101 origin of replication and spectinomycin resistance marker, obtained from Netherlands Culture Collection of Bacteria (NCCB). The E. coil K12 araC gene encoding the transcriptional activator for the araB promoter, and the araB promoter were cloned into pCL1920. The araC-araB region was PCR amplified as a cassette from E. coil strain FM5 (ATCC deposit no. 53911) genomic DNA using primers of SEQ ID NOs:7 and 8. The resulting PCR fragment was digested with AosI and HindIII, and ligated to pCL1920 digested with AosI and HindIII. Plasmid DNA of colonies resulting from transformation was isolated and assayed by restriction digestion and sequencing to confirm the desired construction, called pCL1920ara. A RgTAL coding region DNA fragment was excised from plasmid pKK223-PAL (described in U.S. Pat. No. 6,521,748) by EcoRI, HindIII digestion and ligated into EcoRI, HindIII digested pCL1920ara to give pCL1920ara.mcs.PAL. The transcription termination sequences rrnBT1 and rrnBT2 were PCR amplified from plasmid pTrc99A (Pharmacia Biotech, Amersham, GE Healthcare, Piscataway, N.J.) using primers of SEQ ID NOs: 9 and 10, and digested with HindIII, which cuts at both 5' and 3' ends of the PCR product. The rrnBT1&2 fragment was cloned into the HindIII site of pCL1920ara.mcs.PAL, 3' to the araB promoter to yield plasmid pLH312. This plasmid was converted to a medium copy number plasmid in two steps. First, a linker was inserted by site-directed mutagenesis to replace the HindIII site in pLH312 between the rrnBT2 transcription terminator and the SC101 origin of replication. This linker contains Kpnl, Xbal and Spel sites for the subsequent cloning of the colE1 replication origin. Two complementary oligonucleotides encoding for the linker sequence (SEQ ID No.s 11 and 12 were used to perform a site-directed mutagenesis reaction with pLH312 as template using the Quick Change Site-Directed Mutagenesis Kit (Stratagene, San Diego, Calif.). Upon sequencing confirmation, the new plasmid was named pLH319. The colE1 replication origin and rop (encodes a replication origin protein) gene locus of pBR322 were PCR amplified using primers of SEQ ID NOs: 13 and 14. The resulting 1.8 kb PCR fragment was digested with Sphl and Spel, and ligated with pLH319 which was digested with Sphl and Spel. This yielded plasmid pLH320, which contains the colE1 replication origin in place of SC101 origin. pLH320 was transformed into E. coli K12 strain BW25113 [Lambda-rph-1 laclq rrnBT14 Δ(lacZ)WJ16 hsdR514 Δ(araBAD)AH33 Δ(rhaBAD)LD78) to generate strain DPD5124. A derivative of BW25113 that contained a plasmid was obtained from Professor Barry Warnner at Purdue University. The plasmid, which was temperature sensitive, was cured from the cells by growing at high temperature to provide the BW25113 strain. BW25113 is available as CGSC#7636 from the E. coli Stock Center at Yale University (New Haven, Conn.).

The DNA fragment containing the codon optimized PcTAL coding region was substituted for the fragment encoding RgTAL in pLH320 using EcoRI and HindIII restriction sites, to generate plasmid pLH344 shown in FIG. 1. Plasmid pLH344 was transformed into E. coli K12 strain BW25113 to generate strain DPD5154.

Example 5

Analysis of Arabinose Induced Expression of PcTAL Enzyme

The TAL activity of the DPD5154 strain was analyzed as follows. Fresh colonies were separately inoculated into 5.0 ml of LB medium supplemented with 50 μg/ml spectinomycin and incubated overnight at 37° C. with shaking at 250 rpm. Each culture was then diluted to an optical density ($OD_{600}$) of 0.02 in the LB medium with 50 μg/ml spectinomycin and grown to an $OD_{600}$ of 0.4, before being induced with 0.02% L-arabinose. The induced cultures were incubated for 20 hours at 37° C. with shaking at 250 rpm after which the cells were pelleted by centrifugation at 2,300×g, 4° C. for 30 minutes in a Beckman GS-6R (Fullerton, Calif.) centrifuge. The pellets were re-suspended in 2.0 ml of ice cold 50 mM Tris-HCl, pH 8.5 containing the Protease inhibitor cocktail (Roche, Palo Alto, Calif.), transferred to ice cold 15 ml sterile conical tubes and sonicated in a Fisher Sonic Model 300 Dismembrator (Pittsburgh, Pa.) at 50% power repeating four cycles of 30 seconds sonication with 60 seconds rest in between each cycle. The samples were kept in an ice bath during the entire procedure. Each sonicated sample was centrifuged at 15,000×g for 30 minutes at 4° C. to separate the crude cell extracts into soluble (supernatant) and insoluble (pellet) protein fractions. The resulting pellet was re-suspended in 1.0 ml of ice cold 50 mM Tris, pH 8.5 containing the Protease inhibitor cocktail. The protein concentration of each soluble sample was determined using the Bradford protein assay (Bio-Rad, Hercules, Calif.). Each sample was diluted with 50 mM Tris-HCl, pH 8.5 until the optical density (595 nm) was in the linear range of a bovine serum albumin (BSA) standard curve which ranged from 0.125-1.0 mg/ml. The TAL activity was determined for soluble protein samples by measuring production of pHCA from tyrosine. A 1.0 ml reaction containing 40 μg of soluble protein sample, 100 mM CAPS pH10 buffer and 10 mM tyrosine was monitored in a 1.5 ml UV grade disposable cuvette (VWR) for 3 minutes at 35° C. Absorption at λ315 nm was measured using a Perkin-Elmer Lamba20 spectrophotometer (Wellesley, Mass.) and was converted to U/g of TAL activity as follows:

Total TAL Activity (μmol/min)=Δ315 nm (/min)×1,000,000 (μM/M)/pHCA extinction coefficient ($M^{-1}$ $cm^{-1}$)]=Δ315 nm (/min)×(1,000,000 (μmol/mol)/16,800 $mol^{-1}$ $cm^{-1}$)

TAL Specific Activity (U/g)=Total TAL Activity (μmol/min)/amount of TAL protein used in rxn=Total TAL Activity (μmol/L/min)/0.040(g/L) =Δ315 nm×1480 (U/g)

The TAL activities in the soluble crude extracts of DPD5154 were measured for two clones and results are shown in Table 5. TAL activity was measured in units per gram of soluble proteins as described in General Methods.

TAL activity of strain DPD5124, containing the coding region for non-thermostable RgTAL has a typical TAL activity of 150-230 U/g when measured by the same method. Since both PcTAL and RgTAL activities were expressed at ~50% of total cellular proteins (see data below), the TAL activity of PcTAL is comparable to that of RgTAL. Typically an uninduced culture has negligible TAL activity.

TABLE 5

TAL activity of two replicate clones of DPD5154 strain induced by arabinose.

| Sample | TAL Activity (U/g) |
| --- | --- |
| DPD 5154-1 | 290 |
| DPD 5154-2 | 241 |

The level of TAL protein expression in the DPD5154 strain was assayed as follows: 7.0 kg of each protein sample (soluble and insoluble fractions) was diluted 1:1 with 2× Laemmli protein sample buffer (Bio-Rad, Hercules, Calif.), denatured at 100° C. for 10 min, then loaded onto a 4-12% gradient Bis-Tris gel (Invitrogen) that was run at 200 V for approximately one hour. Each gel was then rinsed with double distilled water for 5 minutes and stained with Simply Blue SafeStain (Invitrogen) for 45 minutes. Stained gels were de-stained by repeated washes with Millipore water while shaking gently until the non-protein background became transparent. The de-staining was typically performed overnight at room temperature with gentle orbital shaking. Images of stained gels were captured using a Kodak Gel Logic 100 imaging system.

Figure 2:
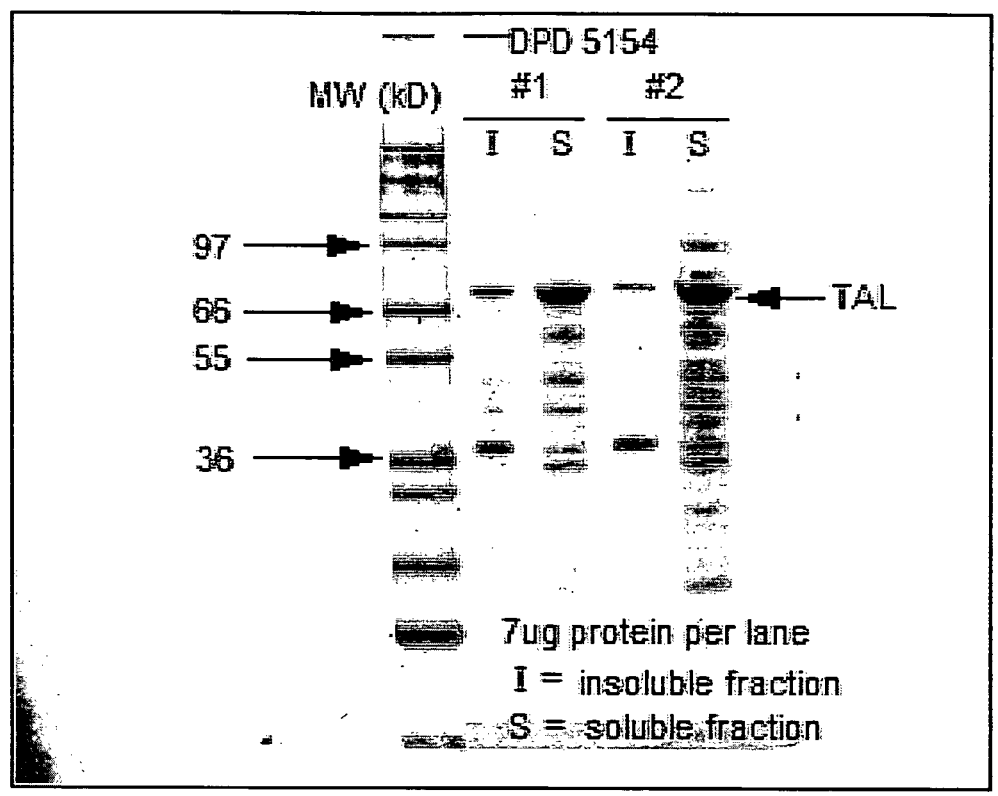
FIG. 2 shows an acrylamide gel of extracts (stained with Simply Blue SafeStain) from E. coli strain DPD5154 with arabinose induced expression of PcTAL.

As can be seen in FIG. 2, a high level of PcTAL protein expression was observed in the soluble fraction, of strain DPD5154 samples. The protein expression level of PcTAL in crude cell extracts was analyzed using the Bioanalyzer (Agilent, Palo Alto, Calif.). The manufacture's procedure was followed, using the protein electrophoresis protocol "Protein 200 Plus". The level of PcTAL protein was estimated to be approximately 50% of total soluble proteins. Very little PcTAL protein was detected in the insoluble fraction.

Example 6

Purification of PcTAL Enzyme from DPD5154 Strain

Cells required for this Example were grown in a 10 liter Braun BiostatC fermentor with an initial volume post inoculation of 8 liters of medium containing: yeast extract (2 g/L), $CaCl_2.2H_2O$ (0.8 g/L), citric acid.$H_2O$ (1.9 g/L), $FeSO_4.7H_2O$ (0.2 g/L), $MgSO4.7H_2O$ (1.1 g/L), $MnSO_4.H_2O$ (0.03 g/L), NaCl (0.01 g/L), $ZnSO_4.7H_2O$ (1.0 mg/L), H3BO3 (0.1 mg/L), $CuSO_4.5H_2O$ (0.1 mg/L), $NaMoO_4.2H_2O$ (0.1 mg/L), phosphoric acid, 85% (2.9 mL/L), sulfuric acid, 98% (0.5 mL/L), KOH, 50% (0.275 mL/L), and antifoam (0.5 mL/L). Prior to inoculation, glucose and spectinomycin were added to final concentrations of 5 g/L and 50 mg/L respectively. The inoculum was grown in a 2 L shake flask containing 500 mL of the following medium: $KH_2PO_4$ (2.0 g/L), $K_2HPO_4$ (13.0 g/L), $(NH_4)_2PO_4$ (4.0 g/L), $MgSO_4.7H_2O$ (1.0 g/L), yeast extract (2.0 g/L), ferric ammonium citrate (0.1 g/L), glucose (5.0 g/L) and spectinomycin (50 mg/L), with pH adjusted to 6.8. The shake flask was incubated at 36° C. and 300 rpm to an $OD_{550}$ of 3 and the entire contents used to inoculate the fermenter. The fermenter was controlled at 36° C., pH 6.8 (with NH4OH, 40% (w/v)), airflow of 4.0 SLPM, pressure of 0.5 barg, and dissolved oxygen tension of 25%. A solution of glucose (50% (w/w)) was fed to the fermenter to maintain a specific growth rate of 0.2 g/g h. When the culture reached an $OD_{550}$ of 35, arabinose was added at a final concentration of 0.3 g/L and the glucose feed rate held at 0.85 g/min for 12 hours until harvest. The final cell density in the recovered broth was an OD$_{550}$ of 92 (30 g/L dry cell weight) and the final volume was 8.7 L.

Figure 3:
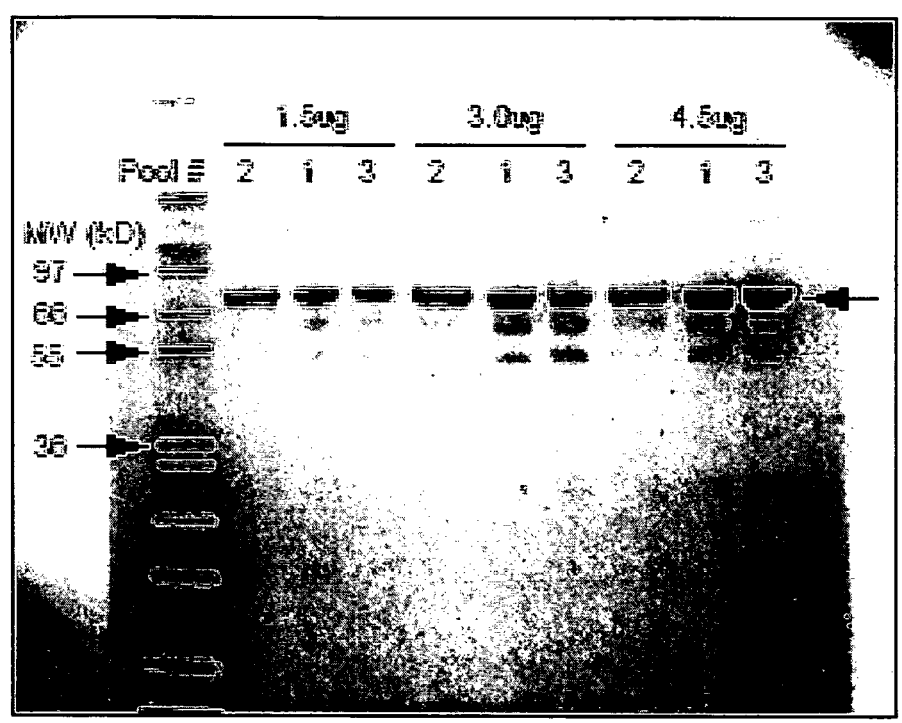
FIG. 3 shows an acrylamide gel of pooled FPLC fractions prepared during purification of the PcTAL enzyme expressed in the DPD5154 strain.

Six grams of cell pellet, from the 10 liter fermentation of DPD5154 was resuspended in 6.0 mL Buffer A (10 mM Tris-HCl, pH 8.0, 200 μM EDTA) containing one EDTA-free protease inhibitor tablet (Roche Biosciences, Palo Alto, Calif.), 1.0 μg/ml Leupeptin, 1.0 μg/ml Pepstatin, 40 μg/ml Bestatin 5.0 mM CA. Cells were lysed by two passes through a French Pressure Cell at 20,000 PSI, and clarified by centrifugation at 12,000×g for 20 minutes. To the clarified supernatant, 1.0% streptomycin sulfate was added, and the suspension was gently mixed for 15 minutes at 4° C. and then clarified by centrifugation at 12,000×g for 20 minutes. The supernatant was heated at 60° C. for 20 min, and centrifuged again at 12,000×g for 20 minutes. This clarified crude extract sample was loaded onto a Q Sepharose FF 16/10 anion exchange column equilibrated with buffer A in an Akta FPLC system (Amersham, GE Healthcare, Piscataway, N.J.), and eluted with 10 column volumes of gradient from Buffer A, to Buffer A containing 1.0 M NaCl. Five ml fractions were collected from the column and assayed for TAL activity as described above. The fractions containing TAL activity were pooled. To the pooled anion exchange fractions containing TAL activity, saturated (NH$_4$)$_2$SO$_4$ (4.0M) was added to final 30% saturation. After centrifugation at 12,000 g for 20 minutes, additional saturated (NH$_4$)$_2$SO$_4$ (4.0M) was added to the supernatant fraction to a final 50% saturation. The mixture was centrifuged again at 12,000 g for 20 minutes, and the supernatant was removed. The pellet was resuspended in 3.0 mL Buffer A with 1.0 M (NH$_4$)$_2$SO$_4$, followed by 6.0 mL Buffer A to dissolve most of the pellet before centrifugation (20,000 g, 20 minutes). The supernatant was then loaded onto a HiPrep 16/10 Phenyl FastFlow FPLC column (Amersham) equilibrated with Buffer A containing 1.0 M (NH$_4$)$_2$SO$_4$, and eluted with a 1.0 to 0 M (NH$_4$)$_2$SO$_4$ gradient. Five ml fractions were collected from the column and assayed for TAL activity as described above. The purity of the PcTAL protein in the fractions was analyzed by SDS-PAGE. The fractions containing TAL activity with high purity as determined by SDS-PAGE were pooled. Samples of pooled fractions from: #1—before the major peak with TAL activity; #2—containing highest TAL activity; and #3—after the major TAL activity peak; were loaded at 1.5 μg, 3.0 μg, and 4.5 μg a shown in FIG. 3. The results indicated high purity of the #2 sample. The pooled fractions containing TAL activity were stored in 25% glycerol at −80° C. and their purity verified by SDS-polyacrylamide gel electrophoresis.

Example 7

Temperature Profiles and Thermostability of PcTAL Enzyme in DPD5154 Strain

A fermentation run was performed as in Example 6 for strain DPD5154. The TAL activity of the strain was measured in a cell-based assay at different temperatures. The fermentation cell paste was resuspended in water, and diluted to OD$_{600}$ of 3.0. Formation of pHCA was monitored in a 1.0 ml reaction in a UV grade disposable cuvette (VWR) for three minutes at λ315 nm, 35° C. with 0.03 OD$_{600}$ of DPD5154 cells, in 100 mM CAPS, pH10 with 10 mM tyrosine. The pH value of the CAPS buffer was adjusted according to the corresponding assay temperature, which was varied from 25° C. to 60° C. The TAL activity was calculated using the following equation based on the assumption that 1.0 OD$_{600}$ of E. coli cells is equivalent to 0.33 g/L dry cell weight (dcw). The extinction coefficient of pHCA at pH 10 at 315 nm had previously been experimentally determined to be 16,800 M$^{-1}$ cm$^{-1}$. One unit of enzyme activity is defined as the formation of 1.0 μM of pHCA product per minute reaction.

The total TAL Activity (μM/min)=Initial Slope (/min)×[1,000,000 (μM/M)/16,800 M$^{-1}$ cm$^{-1}$]= Slope (/min)×59.52 (μM)

$$TAL \text{ Specific Activity}(U/g\ DCW) = \frac{\text{Total } TAL \text{ Activity } (\mu M/min)}{OD_{600} \times 0.33\ g\ dry\ cell/L}$$

Figure 4:
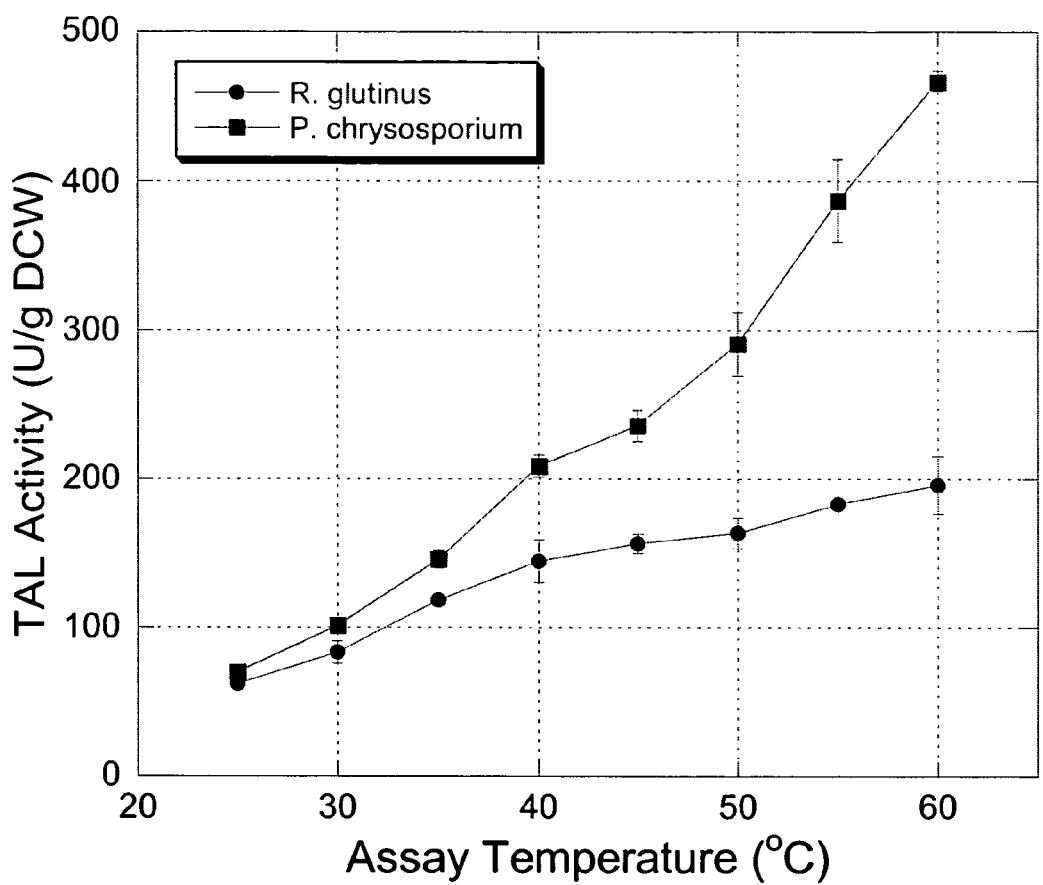
FIG. 4 shows a graph comparing the temperature profiles of the whole cell TAL activity of E. coli strains DPD5124 expressing the RgTAL enzyme and DPD5154 expressing the PcTAL enzyme. The TAL activity was measured in U/g dcw.

The whole cell TAL activity of strain DPD5154 increased significantly as the temperature was raised from 25° C. to 60° C. as show in FIG. 4. At 60° C. (467 U/g dcw) the activity was approximately six times that observed at 25° C. (70 U/g dcw). The maximum TAL activity was observed at 60° C. The temperature profile of strain DPD5124 (RgTAL) is also shown in FIG. 4. RgTAL has similar activity as PcTAL at 25° C. (63 U/g DCW), and its activity increases to 200 U/g DCW at 60° C., which is significantly less increase compared to PcTAL over the same temperature range. These results indicated that the PcTAL enzyme is a highly thermostable enzyme.

Figure 5:
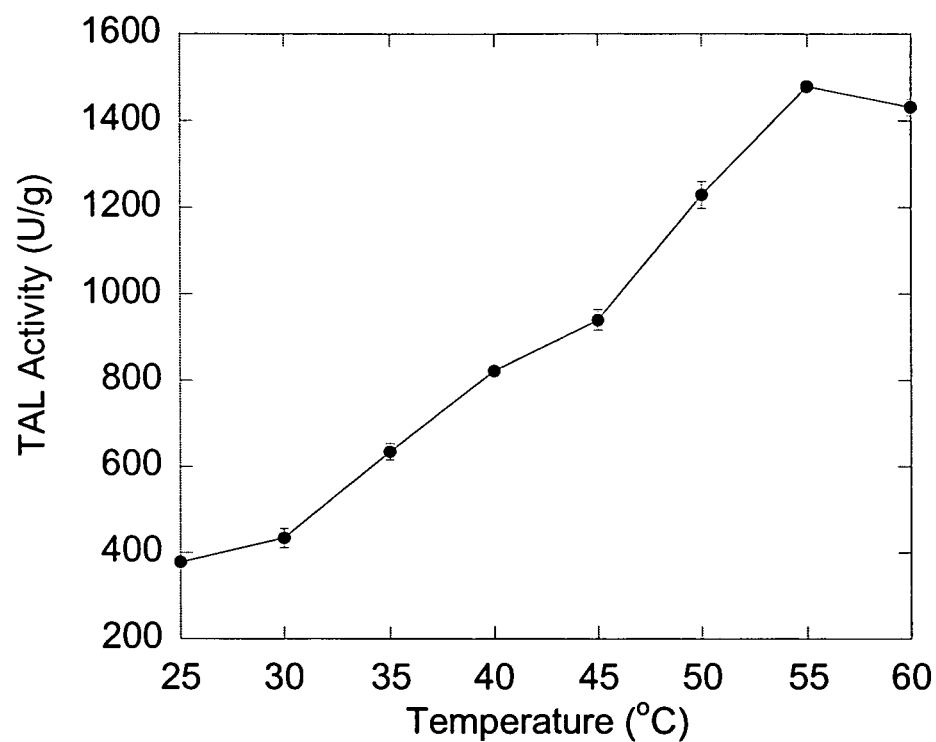
FIG. 5 shows a graph of the temperature profile of the TAL activity of the purified PcTAL enzyme. The TAL activity was measured in U/g (soluble proteins).

The in vitro enzymatic assay using the purified PcTAL was performed as a comparison to the whole cell assay. The temperature profile of the purified PcTAL enzyme (from Example 6) was measured at temperatures varying from 25° C. to 60° C. in 100 mM CAPS buffer, pH 10, containing 1.0 mM tyrosine. The profile, shown in FIG. 5, was similar to that obtained for the whole cells of DPD5154 with the exception that the free enzyme was most active at 55° C., while the enzyme in the whole cells was most active at 60° C. The higher temperature optimum for the whole cell enzyme could be due to the enzyme's protection afforded by the cell membrane and intracellular molecules.

Figure 6:
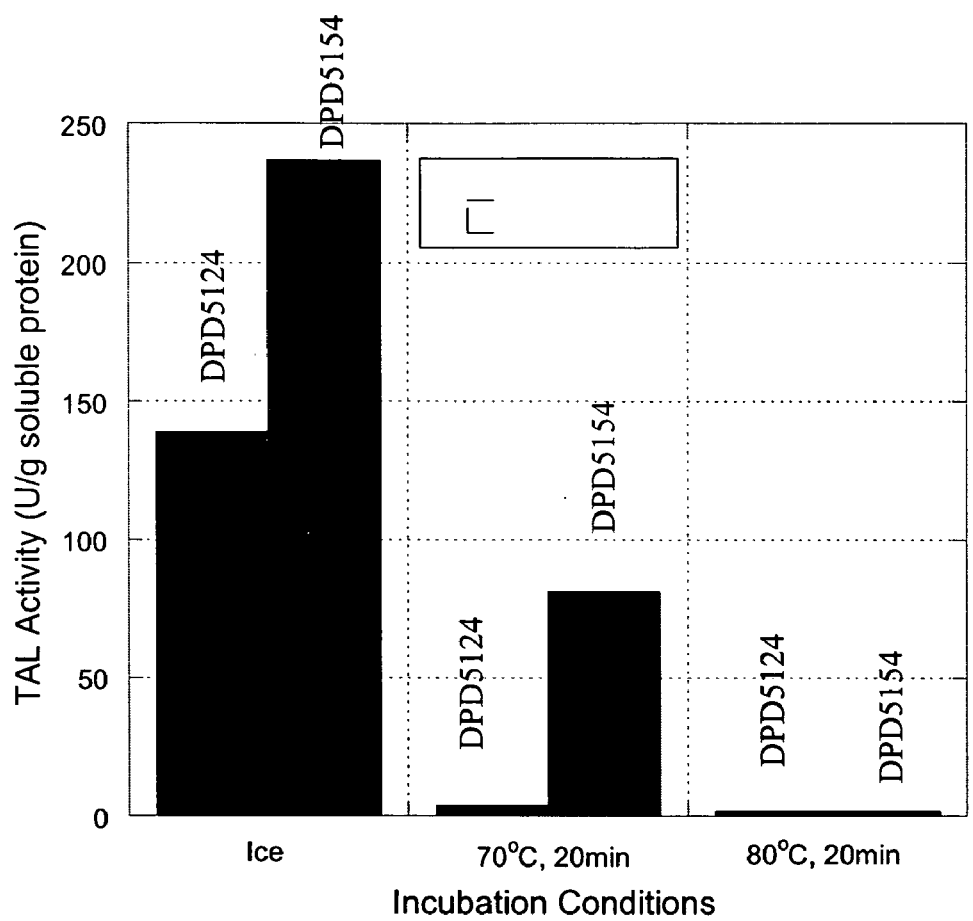
FIG. 6 shows the heat inactivation of TAL activity in crude extracts of DPD5154 strain expressing PcTAL and DPD5124 strain expressing RgTAL. The TAL activity was measured in U/g (soluble proteins).

The stability of TAL activity of PcTAL and RgTAL against heat denaturation was analyzed by extented heat treatment at various temperatures. The crude extracts of DPD5154 (PcTAL) and DPD5124 (RgTAL) strains were generated as described above. After incubation at 70° C. or 80° C. for 20 min in 50 mM Tris-HCl, pH 8.0, the TAL activity of each enzyme was determined and calculated based on soluble proteins in the crude extracts. With DPD5124 extract, 97% of the TAL activity was lost after 20 min at 70° C.; while DPD5154 lost only 34% of its TAL activity under the same conditions. Both extracts lost most activity after 20 min at 80° C. These results shown in FIG. 6 confirmed the thermostability of PcTAL as compared to RgTAL.

Figure 7:
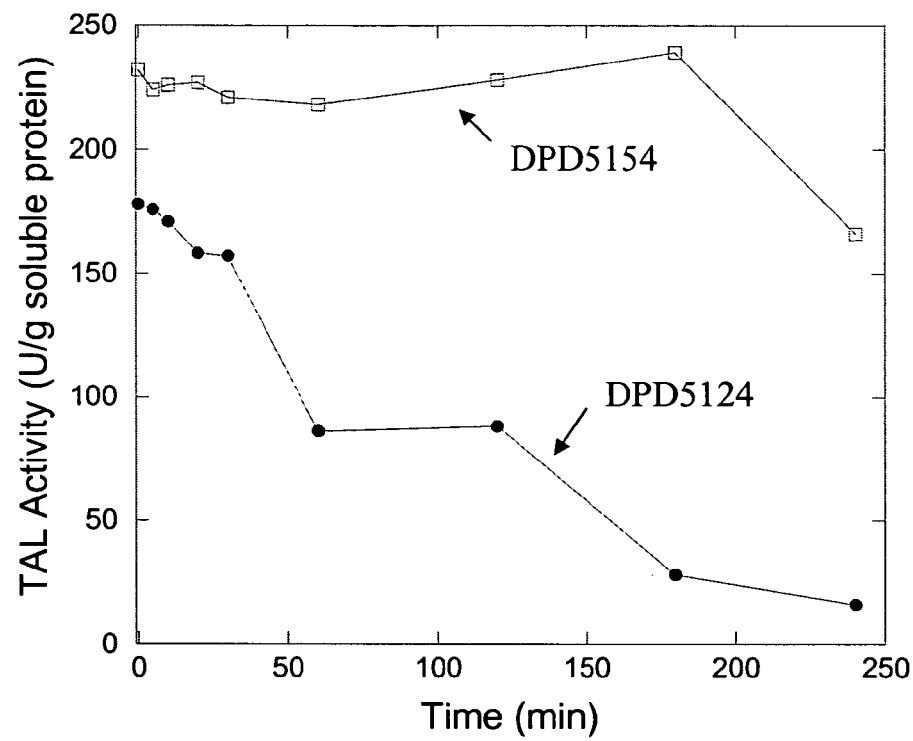
FIG. 7 shows a graph of thermostability of crude extracts of DPD5154 expressing PcTAL versus DPD5124 expressing RgTAL extracts at 60° C. The TAL activity was measured in U/g (soluble proteins).

The thermostability of the PcTAL enzyme was further characterized at 60° C. The crude extracts of DPD5154 (PcTAL) and DPD5124 (RgTAL) strains were incubated at 60° C. in 50 mM Tris-HCl, pH 8.0, and the TAL activities were measured as described previously at several time points up to 4 h. The DPD5154 extract maintained its full TAL activity for 3 h, and retained 72% activity after 4 h, while DPD5154 extract lost 50% of its TAL activity after one hour, and only 9% of the activity remained after 4 h. These results shown in FIG. 7 substantiate the thermostability of PcTAL at 60° C. and at pH 8 as compared to RgTAL.

Example 8

The pH Profile of PcTAL Enzyme at 35° C.

The pH profile of PcTAL activity was determined using purified enzyme prepared as described in Example 6. First, a series of buffers was made at various pH's, including 100 mM Tris-HCl, pH 7.0 to 9.0, 100 mM CAPS, pH 9.5 to 11.5; each buffer was calibrated at 35° C. The TAL reaction, at various pHs at 35° C., was performed using 5.0 μg of PcTAL, and 1.0 mM tyrosine as the substrate. Since the extinction coefficient of pHCA changes over the pH range used in this study (pH 7 to pH 11.5) the extinction coefficient of pHCA at each pH was measured, shown in Table 6, and these values were used to derive the TAL specific activity based on pHCA production at each pH.

TABLE 6

The extinction coefficients of pHCA at various pHs, measured at 35° C.

| pH (35° C.) | Extinction Coefficient ($M^{-1}$ $cm^{-1}$) |
|---|---|
| 7.0 | 11000 |
| 7.5 | 11088 |
| 8.0 | 11613 |
| 8.5 | 12363 |
| 9.0 | 13913 |
| 9.5 | 16625 |
| 10.0 | 17875 |
| 10.5 | 18525 |
| 11.0 | 18563 |
| 11.5 | 18700 |

Figure 8:
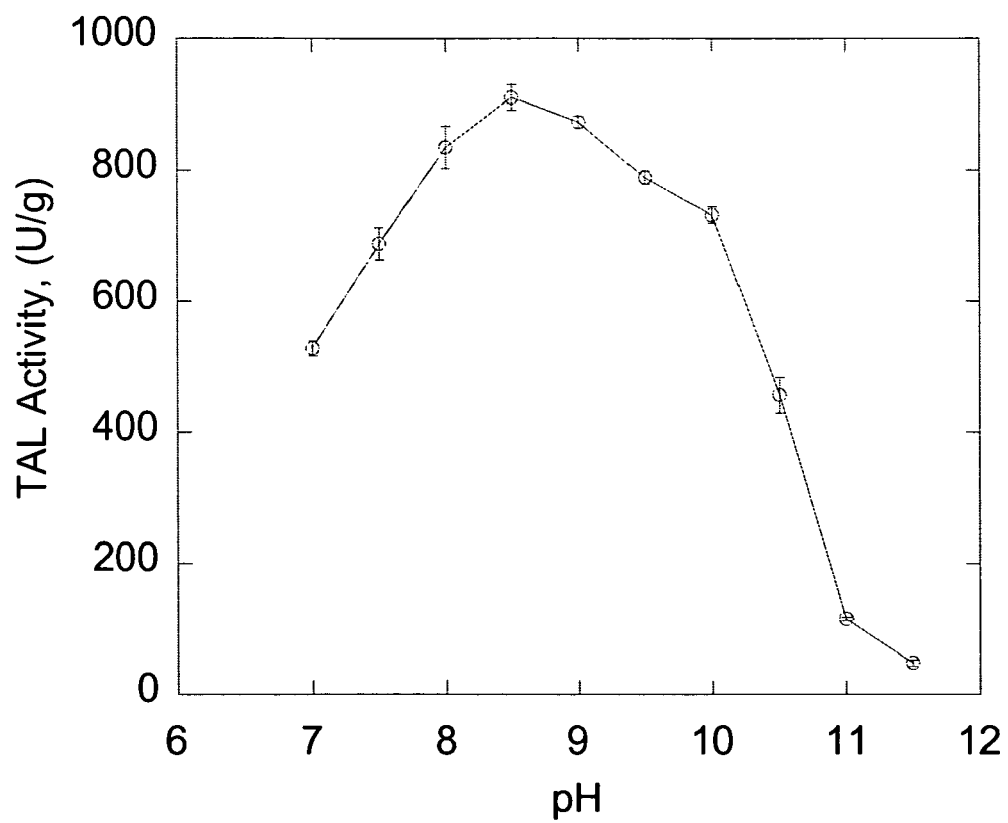
FIG. 8 shows a graph of the pH profile of the PcTAL activity measured at 35° C. The TAL activity was measured in U/g (soluble proteins).

The reaction rate was measured by UV absorbance, as described in Example 5, and TAL activity was calculated based on the measured extinction coefficients, as described in Example 7. The pH profile for PcTAL is shown in FIG. 8. The results indicated that the pH optimum for the PcTAL enzyme at 35° C. was pH 8.5.

Example 9

Characterization of the Kinetic Parameters of the PcTAL Enzyme

The kinetic parameters of the PcTAL enzyme for tyrosine and phenylalanine were determined at 45° C., in 100 mM CAPS, pH 9.5 buffer. The increase of TAL and PAL activities with increasing substrate concentrations followed the typical Michaelis-Menton equation. The $k_{cat}$ of the enzyme was 1.3 $S^{-1}$ for tyrosine, and 3.3 $S^{-1}$ for phenylalanine. The $K_M$ was 44 μM for tyrosine and 161 μM for phenylalanine. The $k_{cat}/K_M$ value was slightly higher for tyrosine (3.0 $M^{-1}$ $S^{-1}$) than for phenylalanine (2.1 $M^{-1}$ $S^{-1}$), indicating the enzyme's slight preference for tyrosine (PAL/TAL ratio of 0.7). The enzyme did not accept histidine as a substrate when an assay containing 20 mM histidine as substrate in 100 mM diethanol amime at pH 9, 1.3 mM 2-mercaptoethanol, and 0.1 mM $MnCl_2$ was used. The substrate specificity of the PcTAL enzyme is therefore similar to other known fungal PAL/TAL enzymes, such as that from *R. glutinis*, with dual specificity for tyrosine and phenylalanine.

Examples 10-13 below are studies that were performed to approximately simulate the real process conditions in a test tube, and obtain data for the optimum pH and temperature for function of cells containing PcTAL under such conditions.

Example 10

Determination of the Optimum Cell Load of PcTAL Strain DPD 5154 for Performing Variable Temperature and pH Experiments Cells for this Example were grown in a 10 liter Braun BiostatC fermentor by the protocol described in Example 6, with a final cell density in the fermentation broth of $OD_{550}$ of 130.92 and volume of 8.7 L. The g dcw/L was determined assuming that 1.0 $OD_{550}$ contained 0.33 g dcw/L: 130.92 $OD_{550}$×0.33 g dcw/L/$OD_{550}$=43.2 g dcw/L.

The fermentation broth was diluted 1:10 with saline solution (8.5 g NaCl/L in $H_2O$, pH titrated to 9.9) to provide a final cell concentration of 4.32 g dcw/L. Dilutions with cell concentrations of 0.5, 1.0 and 2.0 g dcw/L were prepared using the same formula. The cell suspensions were equilibrated to 50° C., titrated to pH 9.9 and stored at 50° C. A 40 mg/mL stock solution of tyrosine at 50° C. at pH 9.9 was prepared in $H_2O$.

The bioconversion of tyrosine to pHCA was performed by adding 5.0 ml of each of the three different dilutions of cell suspensions separately to 5.0 ml of tyrosine solution in a 50 ml tube. The final concentrations of cells for the reaction were: 0.25, 0.5 and 1.0 g dcw/L and the final concentration of tyrosine for all reactions was 20 g/L (110 mM). All reactions were incubated at 50° C. with shaking at 180 rpm.

Samples (1.0 ml) were taken at 30, 60, 90, and 120 minutes after start of the reaction. The samples were centrifuged (14,000 g×~8 minutes), supernatant filtered through a 0.2 μm filter, and the filtrate diluted using 50 mM Tris/HCl, pH 7.5. The whole cell TAL assay was performed by diluting each sample to a final $OD_{600}$ of 1.5. An appropriate volume of assay buffer (100 mM CAPS, pH 10.0) was added to a methyl acrylate cuvette (1.5 ml capacity, VWR Cat. #58017-850) to make up the required final volume (1.0 ml) after accounting for tyrosine and cell suspension addition. Tyrosine (10 μl of 100 mM solution in 200 mM NaOH) was added followed by the required volume of the cells to achieve a final $OD_{600}$ of 0.03. The contents were mixed and placed in a spectrophotometer (at 35° C.). The $OD_{315}$ was observed for approximately 3-4 minutes or until a linear increasing line was obtained for 1.0 minute. The specific activity was calculated for each cell concentration, and is given in Table 7.

TABLE 7 pHCA production at 50° C. in samples with different cell concentrations

| Cell concentration (g dcw/L) | Specific activity at 50° C. (g pHCA/g dcw/L/h) |
|---|---|
| 0.25 | 0.761 |
| 0.5 | 0.734 |
| 1.0 | 1.002 |
| average | 0.833 |

As expected, the reaction rate of conversion of tyrosine to pHCA increased with an increase in cell concentration. Since an increase in the rate of the reaction is anticipated with an increase in the temperature and pH, 0.5 g dcw/L was chosen as the cell concentration for further temperature and pH variation studies.

Example 11

Effect of a Wide Range of Temperatures (34° C.-59° C.) on Bioconversion of Tyrosine to pHCA by PcTAL of Strain DPD 5154

A suspension of DPD5154 cells in ~75 ml of saline solution (8.5 g NaCl/L) with a cell concentration at an $OD_{550}$ of 221.47 was used. The desired $OD_{550}$ of 2.998 (0.989 g dcw/L) was achieved through serial dilution of the original sample. The cell suspension was equilibrated to 50° C., titrated to pH 9.9 and stored at 50° C. A tyrosine stock of 40 g/L at pH 9.9 was also prepared and stored at 50° C. Reactions measuring bioconversion of tyrosine to pHCA by the cell suspension were carried out at the following temperatures: 34° C., 39° C., 47° C., and 59° C. Each reaction was initiated by adding 5.0 ml of the cell suspension to 5.0 ml of the 40 g/L tyrosine solution in a 50 ml disposable conical tube. The final concentration of cells in each reaction was 0.5 g dcw/L. The final concentration of tyrosine in each reaction was 20 g/L (110 mM). All reactions were incubated at the temperatures indicated above with shaking at 180 rpm. Samples (750 µl) were taken at 30, 60, 90, 120 minutes, centrifuged (14,000×g for ~8 minutes), the supernatants filtered through 0.2 um filters (Costar #8161), and the filtrates diluted using 50 mM Tris/HCl, pH 7.5. The filtrates were analyzed by HPLC for the amount of pHCA as described in General Methods. Table 8 summarizes the results obtained. The optimum reaction temperature among those temperatures tested was determined to be 39° C., and the reaction slowed down dramatically at 59° C.

TABLE 8

Effect of temperatures from 34° C.-59° C. on pHCA formation by PcTAL

| Temperature (° C.) | pHCA (mM) formed in 2 h |
|---|---|
| 34 | 5.0 |
| 39 | 6.2 |
| 47 | 4.7 |
| 59 | 0.02 |

Example 12

Effect of Temperatures between 38° C. and 44° C. on Bioconversion of Tyrosine to pHCA by Strain DPD 5154

To determine the optimum temperature between 38° C. and 44° C. for pHCA bioconversion with PcTAL an experiment was performed as in Example 11 with the exception that the temperatures used were: 38° C., 40° C., 42° C., and 44° C. Duplicate reactions for each incubation temperature were initiated by adding 5.0 ml of cell suspension to 5.0 ml of the 40 g/L tyrosine solution. All reactions were incubated with shaking at 180 rpm. Samples (750 µl) were taken at 30, 60, 90, 120 minutes and centrifuged (14,000×g for ~8 min). The supernatants were placed at 85° C. for 20 minutes (to kill the enzyme) and then filtered through 0.2 µm filters (Costar #8161) and diluted using 50 mM Tris/HCl, pH 7.5. The filtrates were analyzed by HPLC for the amount of pHCA.

The results summarized in Table 9 show an increase in pHCA formation with increases in temperature. A plateau in the amount of pHCA formed was not obtained indicating that, under these experimental conditions, the optimum temperature for the reaction was at or above 44° C.

TABLE 9

Effect of temperatures from 38° C.-44° C. on pHCA formation by strain DPD 5154.

| Temperature (c.) | pHCA (mM) formed in 2 h |
|---|---|
| 38 | 1.064 |
| 40 | 1.256 |
| 42 | 1.349 |
| 44 | 1.677 |

Example 13

Effect of Various pHs on Bioconversion of Tyrosine to pHCA with Strain DPD5154 at 42° C.

To determine the optimum pH (between pH 9.8-11.0) for the bioconversion reaction of tyrosine to pHCA at 42° C. using strain DPD5154, reactions were performed as described in Example 11. Tyrosine solutions (40 g/L concentration) were titrated to pH 9.8, 10.0, 10.2, 10.5, and 11.0 and stored at 42° C. Reactions were initiated by adding 5.0 ml of cell suspension to 5.0 ml of each tyrosine solution in a 50 ml disposable conical tube. The final concentration of cells in each reaction was 0.5 g dcw/L and the final concentration of tyrosine was 20 g/L (110 mM). Reactions were incubated at 42° C. with shaking at 180 rpm. Results summarized in Table 10 indicate that at 42° C., the highest rate of reaction (5.9 mM pHCA at 120 minutes) was achieved at pH 9.8-10.0. The reaction performed at pH 10.2 showed an approximate 37% decrease in pHCA formation as compared to the amount of pHCA formed at pH 9.8.

TABLE 10

Effect of various pHs from 9.8-11 on pHCA formation by strain DPD5154 in two h at 42° C.

| pH | pHCA (mM) formed in 2 h |
|---|---|
| 9.8 | 6.04 |
| 10 | 5.93 |
| 10.2 | 3.75 |
| 10.5 | 0.85 |
| 11.0 | 0.01 |

Based on the above data the recommended temperature and pH for single use of the PcTAL in strain DPD5154 is between about 42° C. and 45° C., with a pH between about 9.9 and 10.1.

Example 14

Conversion of Tyrosine to pHCA Using PcTAL at Different Temperatures and Cell Concentrations in 3 L Applikon BioReactors The following experiment was performed in an Applikon BioReactor (9.0 liter working volume) where pH and temperature of the reaction were controlled. Both strains DPD5154 and DPD5124 were tested. The *E. coli* DPD5154 (PcTAL) cells were produced by the protocol described in Example 6, with a final cell density of 123 $OD_{550}$ 123. In the case of E. coli DPD5124 (RgTAL) the inoculum was grown in a 2.0 L shake flask containing 500 ml of the following medium (in grams per liter) $KH_2PO_4$ (2.0 g/L), $K_2HPO_4$ (13.0 g/L), $(NH_4)_2HPO_4$ 94.0 g/L), $MgSO_4.7H2O$ (1.0 g/L), yeast extract (2.0 g/L), Ferric Ammonium Citrate (0.1 g/L). The pH was adjusted to 7.0 and the medium steam sterilized. Glucose (30.0 g/L) and ampicillin (50 mg/L) were added post-sterilization. The culture was grown in 2 L flasks with 500 mL medium, at 35° C. to about $OD_{550}$ of 2.0 and then the entire contents was used to inoculate the fermentor. The fermentor was controlled at 36° C., pH 6.8, with the dissolved oxygen (DO) tension of 25% controlled with cascade of agitation and air flow with agitation from 400 to 1000 rpm and airflow from 2 to 16 SLPM. The overhead pressure was 0.5. When the glucose level reached below 4.0 g/L a glucose feed program with 60% glucose (w/w) was initiated, consisting of: first 4 h at 0.36 g/min, next 12 h at 0.73 g/min and to the end of run at 0.56 g/min. When the culture reached an $OD_{550}$ of 35, arabinose was added to final concentration of 0.5 g/L The fermentation was terminated 20 h after arabinose addition. The final cell density in the fermentation broth was an $OD_{550}$ of 90 and the final volume was about 9 liter. The g dcw/L was determined assuming that 1.0 $OD_{550}$ contained 0.33 g dcw/L:=30 g dcw/L.

The cells were harvested by centrifugation and stored as a frozen paste at −80° C. until use. Before use, the cell paste was thawed and suspended in the saline solution to about 10% w/v. The cells were added at concentrations that vary from 2 to 13 g dry cells per liter as given in Tables 9 and 10. The cell dry weight concentration was calculated from [cells wet weight]×[% solids] where [% solids] was determined after drying the cells in a vacuum oven, at 90° C. for >16 h.

The tyrosine used was AR grade (J. T. Baker). It was suspended in distilled, deionized water at 33% w/w concentration, homogenized in a blender and added to about 50 g/L final concentration. Reactions were conducted in 3 L Applikon BioReactors (Applikon, De Brauwweg 13, The Netherlands), with a 1-2 L working volume. The set points for the control systems were pH 9.9 with automatic addition of NaOH 25% w/v with agitation at 400 rpm. The temperatures tested were 30° C., 35° C., 40° C., 43° C., 45° C. or 48° C. as given in Tables 9 and 10. The bioconversion was typically done by adding the tyrosine suspension to the appropriate concentration, adjusting the pH and temperature to the determined set point, adding the cell suspension to the appropriate concentration, and DI water to the final volume.

Table 11 shows results of studies with the DPD5154 strain, expressing the thermostable PcTAL. In all cases about 50 g/L of tyrosine was converted to 41-42 g/L of pHCA.

Rows 1-6 show the effect of temperature. Varying the temperature from 30° C. to 48° C. increased pHCA volumetric productivity from 2.2 to 7.0 g pHCA/L/h and pHCA specific productivity from 0.37 to 1.17 g pHCA/g cells/h. Thus a shorter time period was required to reach production of 41-42 g/L pHCA at higher temperatures. It took less than half the time to reach 41-42 g/L pHCA at 40° C. than at 35° C.

TABLE 11

Bioconversion with thermostable PcTAL

| Row | Run | Temp C. | Cell conc g/L | Reaction time h | pHCA g/L | Prod g/L-h | Prod g/g-h |
|---|---|---|---|---|---|---|---|
| 1 | pHCA023 | 30 | 6 | 19 | 41.8 | 2.20 | 0.37 |
| 2 | pHCA017A | 35 | 6 | 15 | 41.78 | 2.79 | 0.46 |
| 3 | pHCA011 | 40 | 6 | 7 | 41.6 | 5.94 | 0.99 |
| 4 | pHCA013 | 43 | 6 | 6 | 41.4 | 6.90 | 1.15 |
| 5 | pHCA012 | 45 | 6 | 6 | 41 | 6.83 | 1.14 |
| 6 | pHCA014 | 48 | 6 | 6 | 42 | 7.00 | 1.17 |
| 7 | pHCA015 | 45 | 2 | 19 | 42.2 | 2.22 | 1.11 |
| 8 | pHCA016 | 45 | 4 | 10 | 41.8 | 4.18 | 1.05 |
| 9 | pHCA012 | 45 | 6 | 6 | 41 | 6.83 | 1.14 |

Rows 7-9 show the effect of varying cell concentrations from 2 to 6 g/L at 45° C. There was increased pHCA volumetric productivity from 2.2 to 6.83 g pHCA/L/h.

The non-thermostable RgTAL (strain DPD5124) shows low productivity at 40-48° C. due to RgTAL enzyme rapid deactivation. pHCA production with RgTAL was studied at 30° C. and 35° C. As shown in Table 12 to achieve the same level of pHCA volumetric productivity and specific productivity, twice the concentration of cells (compared to PcTAL) had to be used.

Thus the use of thermostable TAL allowed production of pHCA at higher temperatures and with half the amount of biocatalyst.

TABLE 12

Bioconversion with non-thermostable TAL strain DPD5124

| Row | Run | Temp C. | Cell conc. | Reaction time h | pHCA g/L | pHCA g/L-h | pHCA g/g-h |
|---|---|---|---|---|---|---|---|
| 1 | AP-2005-2 | 30 | 13 | 16 | 44.4 | 2.78 | 0.21 |
| 2 | AP-2005-1a | 35 | 13 | 8 | 45.4 | 5.68 | 0.44 |
| 3 | AP-2005-1b | 35 | 13 | 8 | 44.4 | 5.55 | 0.43 |

What is claimed is:

1. A method for the production of para-hydroxycinnamic acid comprising:
   (a) providing a thermostable tyrosine ammonia lyase enzyme;
   (b) contacting the enzyme of (a) with tyrosine wherein para-hydroxycinnamic acid is produced; and
   (c) optionally recovering said para-hydroxycinnamic acid;
   Wherein the thermostable tyrosine ammonia lyase enzyme is encoded by an isolated nucleic acid molecule selected from the group consisting of:
   (i) an isolated nucleic acid molecule encoding the amino acid sequence as set forth in SEQ ID NO:1;
   (ii) an isolated nucleic acid molecule that hybridizes with (i) under the following hybridization conditions: 0.1× SSC, 0.1% SDS, 6500 and washed with 2×550, 0.1% SOS followed by 0.1×SSC, 0.1% SDS; and
   (iii) an isolated nucleic acid molecule that encodes a polypeptide having 95% identity based on the Clustal method of alignment when compared to a polypeptide having the sequence as set forth in SEQ ID NO:1.

2. A method for the production of para-hydroxycinnamic acid comprising:
   a) providing a recombinant host cell comprising a genetic construct encoding a thermostable tyrosine ammonia lyase enzyme operably linked to a regulated promoter wherein the regulated promoter is responsive to an inducer;
   b) growing the recombinant host cell of (a) in the presence of the inducer and under conditions whereby the tyrosine ammonia lyase enzyme is produced; and
   c) contacting the recombinant host cell of (b) containing the tyrosine ammonia lyase enzyme with tyrosine wherein pHCA is produced;
   Wherein the thermostable tyrosine ammonia lyase enzyme is encoded by an isolated nucleic acid molecule selected from the group consisting of:
   (i) an isolated nucleic acid molecule encoding the amino acid sequence as set forth in SEQ ID NO:1;
   (ii) an isolated nucleic acid molecule that hybridizes with (i) under the following hybridization conditions: 0.1× SSC, 0.1% SOS, 65° C. and washed with 2×SSC, 0.1% SOS followed by 0.1×SSC, 0.1% SDS; and
   (iii) an isolated nucleic acid molecule that encodes a polypeptide having 95% identity based on the Clustal method of alignment when compared to a polypeptide having the sequence as set forth in SEQ ID NO:1.

3. A method according to claim 2 wherein the contacting step (c) is performed at a temperature of about 35° C.

4. A method for the production of para-hydroxycinnamic acid comprising:
   a) providing a recombinant host cell comprising:
      i) a genetic construct encoding a thermostable tyrosine ammonia lyase enzyme operably linked to a regulated promoter wherein the regulated promoter is responsive to an inducer; and
      ii) an endogenous source of tyrosine;
   b) growing the recombinant host cell of (a) under conditions wherein tyrosine is produced; and
   c) contacting the host cell of (a) with the inducer whereby tyrosine ammonia lyase produced, and pHCA is formed;
   Wherein the thermostable tyrosine ammonia lyase enzyme is encoded by an isolated nucleic acid molecule selected from the group consisting of:
   (i) an isolated nucleic acid molecule encoding the amino acid sequence as set forth in SEQ ID NO:1;
   (ii) an isolated nucleic acid molecule that hybridizes with (i) under the following hybridization conditions: 0.1× SSC, 0.1% SDS, 65° C. and washed with 2×SSC, 0.1% SOS followed by 0.1×SSC, 0.1% SOS; and
   (iii) an isolated nucleic acid molecule that encodes a polypeptide having 95% identity based on the Clustal method of alignment when compared to a polypeptide having the sequence as set forth in SEQ ID NO:1.

5. A method according to claim 4 wherein the contacting step (c) is performed at a temperature of about 35° C.

6. A method for the production of para-hydroxycinnamic acid comprising:
   a) providing a recombinant host cell comprising a genetic construct encoding a thermostable tyrosine ammonia lyase enzyme operably linked to a regulated promoter wherein the regulated promoter is responsive to an inducer;
   b) providing a tyrosine producing cell;
   c) co-fermenting the recombinant host cell of (a) with the tyrosine producing cell of (b) under conditions where tyrosine is produced;
   d) contacting the co-fermented cells of (c) with the inducer whereby tyrosine ammonia lyase is produced and pHCA is formed;

Wherein the thermostable tyrosine ammonia lyase enzyme is encoded by an isolated nucleic acid molecule selected from the group consisting of:
(i) an isolated nucleic acid molecule encoding the amino acid sequence as set forth in SEQ ID NO:1;
(ii) an isolated nucleic acid molecule that hybridizes with (i) under the following hybridization conditions: 0.1× SSC, 0.1% SDS, 65° C. and washed with 2×SSC, 0.1% SOS followed by 0.1×SSC, 0.1% SDS; and
(iii) an isolated nucleic acid molecule that encodes a polypeptide having 95% identity based on the Clustal method of alignment when compared to a polypeptide having the sequence as set forth in SEQ ID NO:1.

7. A method of claim 6 wherein the contacting step (d) occurs at a temperature of about 35° C.

8. A method according to either of claims 1 or 2 wherein the isolated nucleic acid molecule is selected from the group consisting of SEQ ID NO:3 or SEQ ID NO:4.

9. A method according to any one of claims 2, 4 or 6 wherein the regulated promoter is selected from the group consisting of araB, rhaB, tetracycline promoter, trp promoter, luxR promoter, tightly regulated synthetic promoters derived from lac/tac promoters, and lnt/att-mediated gene inversion-controlled promoters.

10. A method according to any one of claims 3, 5 or 7 wherein the temperature of at least 35° C. is in a range of about 35° C. to about 60° C.

11. A method according to any one of claims 3, 5 or 7 wherein the temperature of at least 35° C. is in a range of about 40° C. to about 50° C.

12. A method according to anyone of claims 1, 4 or 6 wherein pHCA is produced in the presence of tyrosine ammonia lyase enzyme at alkaline pH.

13. A method according to claim 12 wherein the alkaline pH is in a range from about 8.0 to about 11.0.

14. A method according to claim 13 wherein the alkaline pH is in a range from about 9.5 to about 9.8.

15. A method according to anyone of claims 2, 4, or 6 wherein the recombinant host cell is selected from the group consisting of bacteria, yeasts, filamentous fungi and plants.

16. A method according to claim 15 wherein the host cell is a bacteria selected from the group consisting of *Escherichia, Salmonella, Bacillus, Acinetobacter, Streptomyces, Methylobacter, Rhodococcus, Pseudomonas, Rhodobacter, Synechocystis, Saccharomyces, Zygosaccharomyces, Kluyveromyces, Candida, Hansenula, Debaryomyces, Mucor, Pichia Torulopsis, Aspergillus* and *Arthrobotrys*.

17. A method of claim 16 wherein said recombinant cell is an *E. coli*.

18. A method of claim 17 wherein said *E. coli* cell is of the strain BW25113.

19. A method according to claim 2 wherein the recombinant cell of step (b) expressing the tyrosine ammonia lyase enzyme is optionally harvested and stored prior to the contacting with tyrosine.

20. A recombinant host cell comprising a thermostable tyrosine ammonia lyase enzyme wherein said enzyme is encoded by an isolated nucleic acid molecule selected from the group consisting of:
(a) an isolated nucleic acid molecule encoding the amino acid sequence as set forth in SEQ ID NO:1;
(b) an isolated nucleic acid molecule that hybridizes with (a) under the following hybridization conditions: 0.1× SSC, 0.1% SDS, 65° C. and washed with 2×SSC, 0.1% SDS followed by 0.1×SSC, 0.1% SDS; and
(c) an isolated nucleic acid molecule that encodes a polypeptide having 95% identity based on the Clustal method of alignment when compared to a polypeptide having the sequence as set forth in SEQ ID NO:1.

21. The recombinant host cell of claim 20 wherein the isolated nucleic acid molecule is operably linked to regulated promoter.

22. The recombinant host cell of claim 21 wherein the regulated promoter is selected from the group consisting of araB, rhaB, tetracycline promoter, trp promoter, luxR promoter, tightly regulated synthetic promoters derived from lac/tac promoters, and lnt/att-mediated gene inversion-controlled promoters.

23. The recombinant host cell of claim 20 wherein said recombinant cell is an *E. coli*.

* * * * *